United States Patent [19]
Higgs, Jr. et al.

[11] Patent Number: 5,885,841
[45] Date of Patent: Mar. 23, 1999

[54] SYSTEM AND METHODS FOR QUALITATIVELY AND QUANTITATIVELY COMPARING COMPLEX ADMIXTURES USING SINGLE ION CHROMATOGRAMS DERIVED FROM SPECTROSCOPIC ANALYSIS OF SUCH ADMIXTURES

[75] Inventors: Richard E. Higgs, Jr., New Palestine; Randall K. Julian, Jr., Indianapolis; Raymond E. Kaiser, Jr., Carmel, all of Ind.

[73] Assignee: Eli Lilly and Company, Indianapolis, Ind.

[21] Appl. No.: 712,540

[22] Filed: Sep. 11, 1996

[51] Int. Cl.$^6$ .................................................. G01N 30/72
[52] U.S. Cl. .............................. 436/89; 436/86
[58] Field of Search ........................ 436/89, 86

[56] References Cited

U.S. PATENT DOCUMENTS 5,246,865  9/1993  Stolowitz ................................. 436/89

OTHER PUBLICATIONS

J. E. Biller and K. Biemann, Department of Chemistry Massachusetts Institute of Technology; Cambridge, Massachusetts; Analytical Letters; 515; "Reconstructed Mass Spectra, A Novel Approach For The Utilization Of Gas Chromatograph—Mass Spectrometer Data"; 1974.

*Primary Examiner*—Scott W. Houtteman
*Attorney, Agent, or Firm*—Michael T. Bates

[57] ABSTRACT

System for analyzing a protein sample, comprising a reactor vessel, a chromatographic column, a mass spectrometer, and a computer system. The reactor vessel comprises an enzyme activity capable of digesting the protein sample in order to provide a plurality of peptide digests, an inlet port for receiving the protein to be digested, and an exit port for discharging the peptide digests. The chromatographic column comprises a chromatographic medium capable of chromatographically fractionating the peptide digests as the peptide digests are eluted through the column, wherein the chromatographic column comprises an inlet port for receiving the peptide digests, said inlet port being in flow communication with the exit port of the reactor vessel, and wherein the chromatographic column comprises an exit port for discharging an effluent comprising the chromatographically fractionated peptide digests. The mass spectrometer is capable of generating a mass spectroscopic data set comprising data from which a first plurality of selective ion chromatograms for the fractionated peptide digests can be generated. The mass spectrometer has an inlet port for receiving the chromatographically fractionated peptide digests. The inlet port is in flow communication with the exit port of the chromatographic column. The computer system is operationally coupled to the mass spectrometer such that the computer system is capable of analyzing the mass spectroscopic data set. The computer system comprises programming enabling the computer system to analyze protein samples using selective ion chromatograms derived from the mass spectroscopic data set.

55 Claims, 5 Drawing Sheets

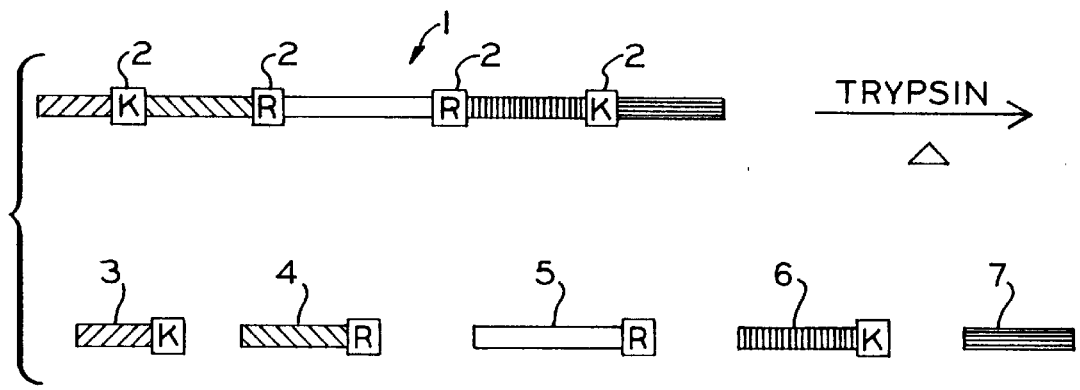
FIG_1
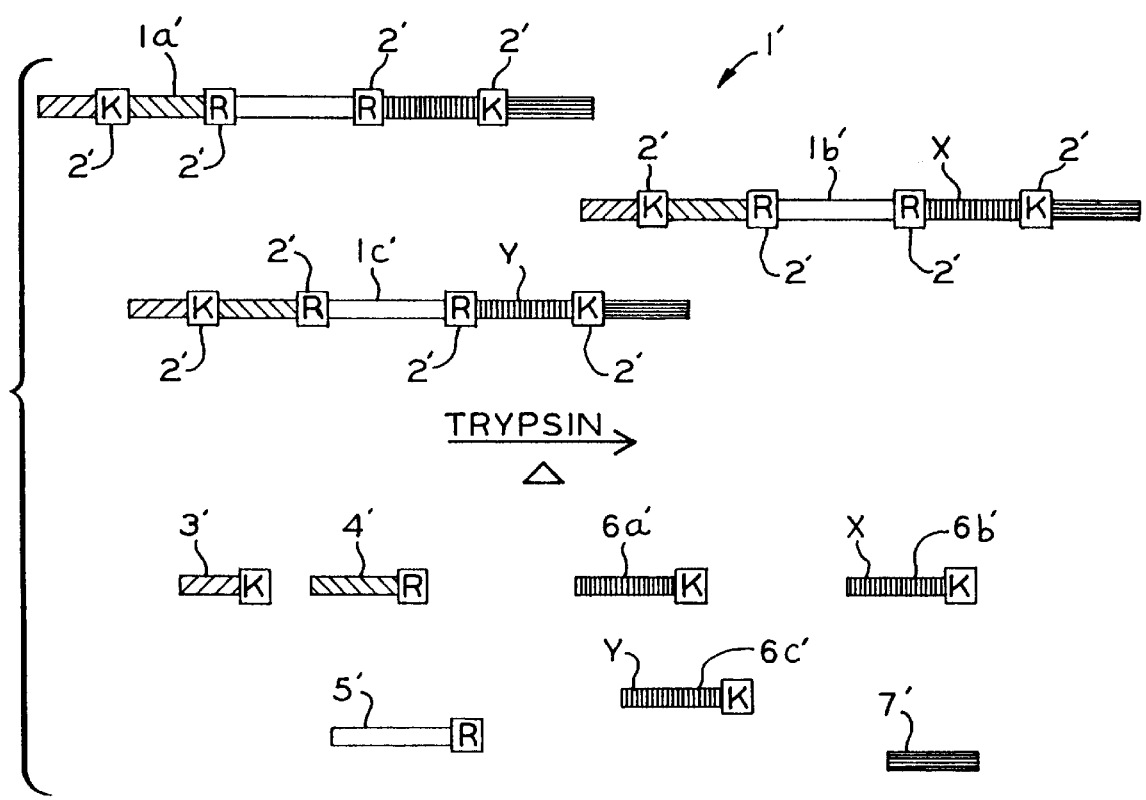
FIG_2

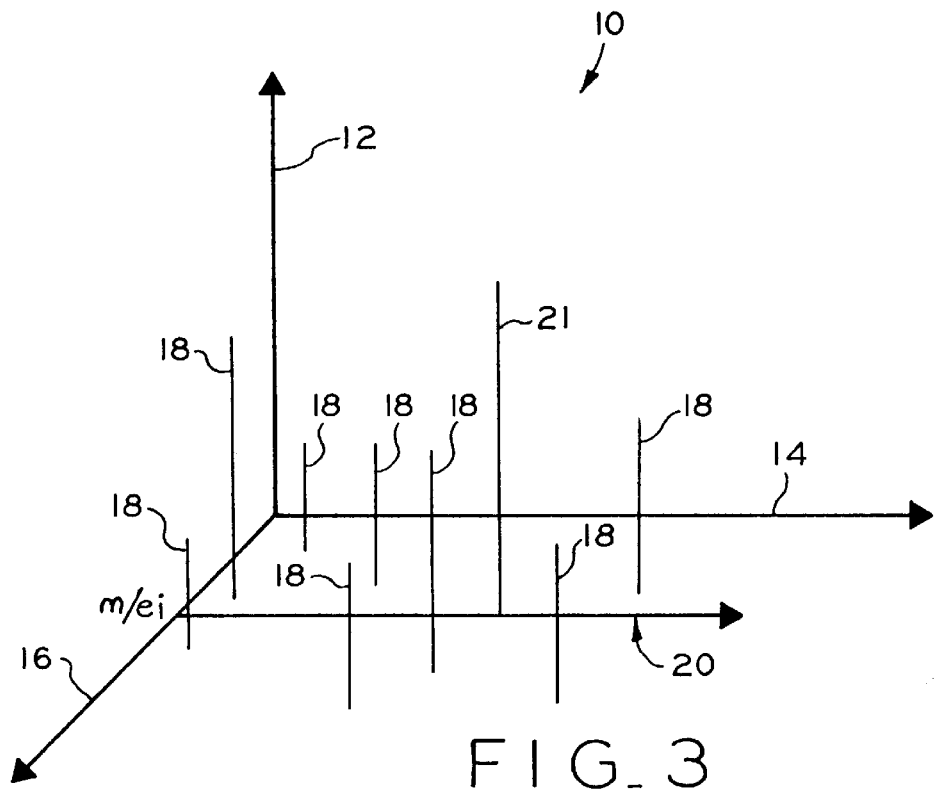
FIG_3
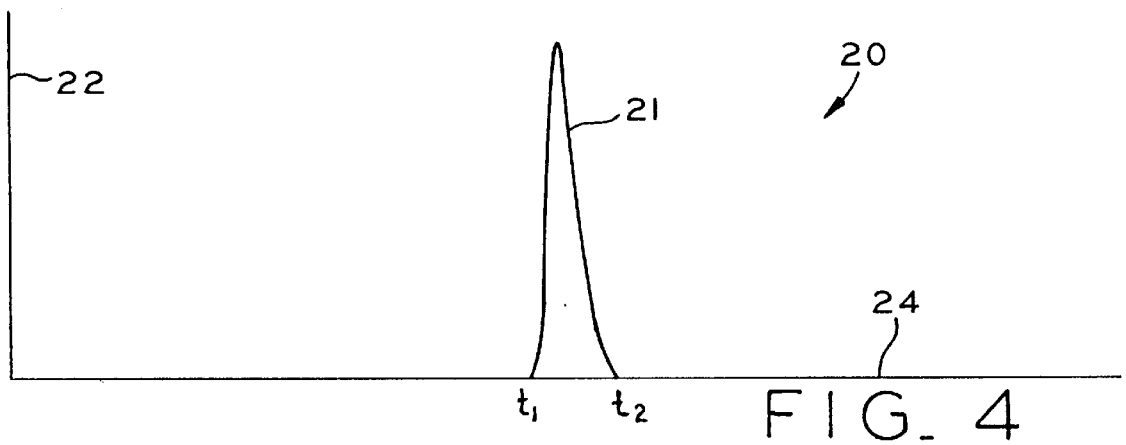
FIG_4
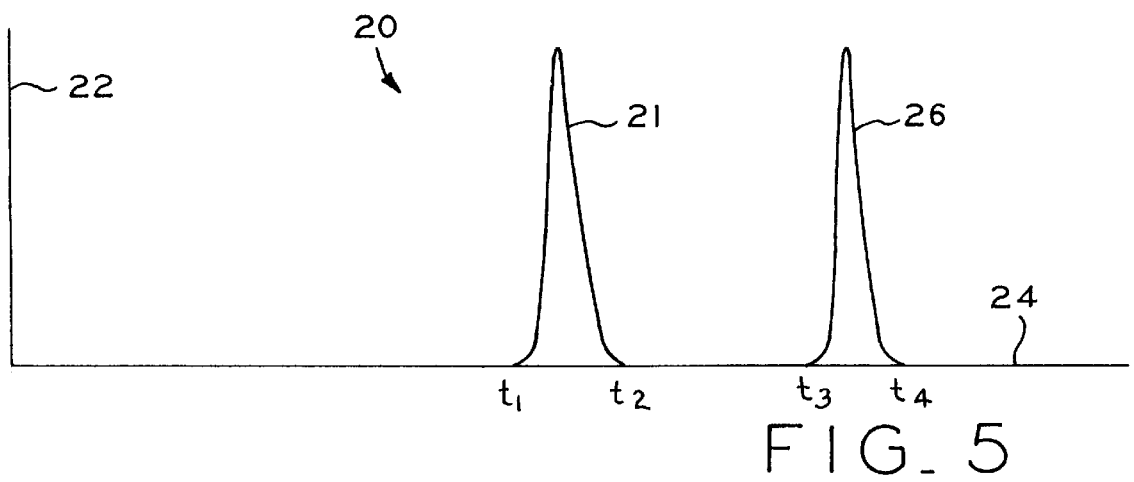
FIG_5

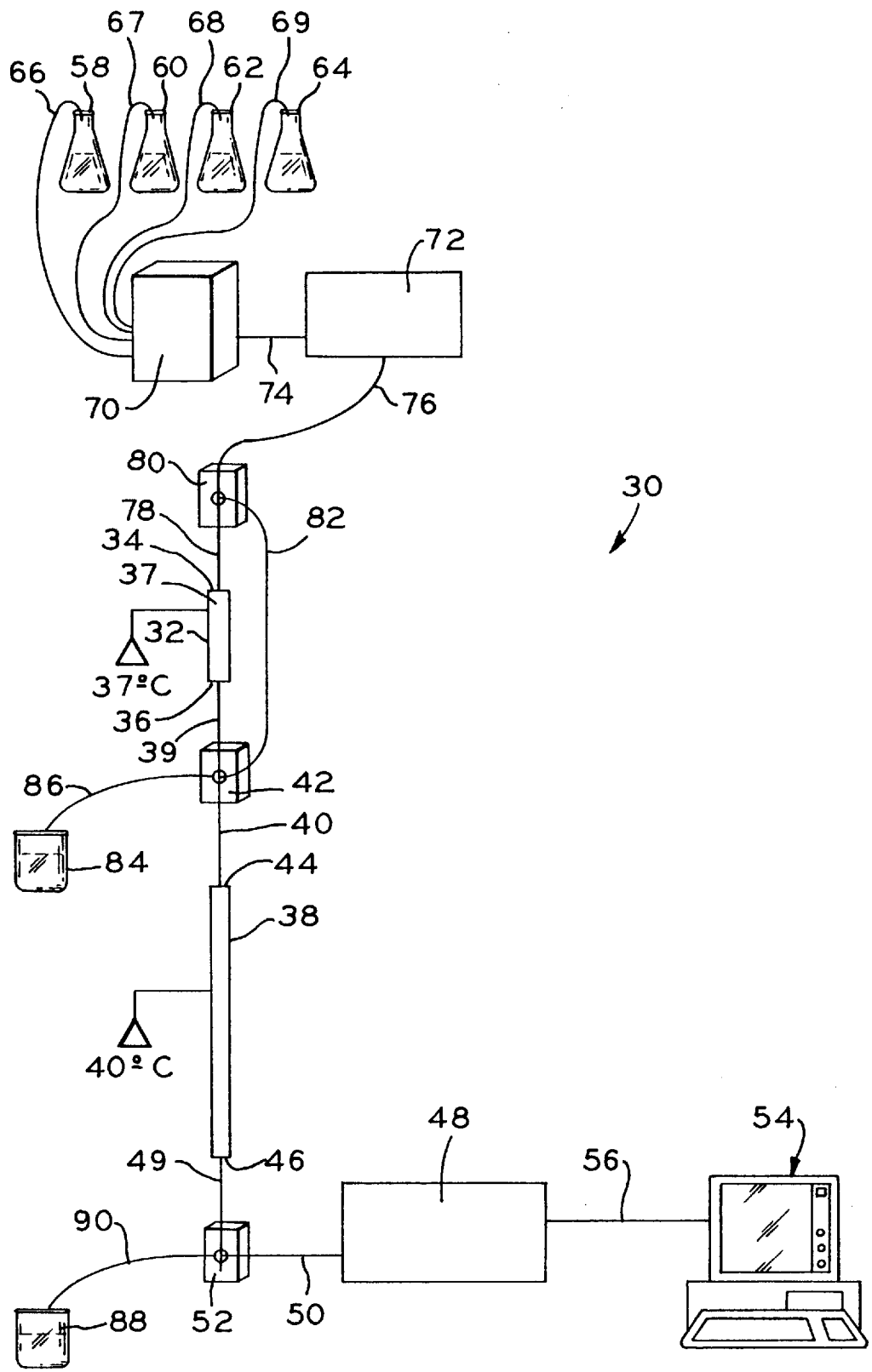
FIG_6

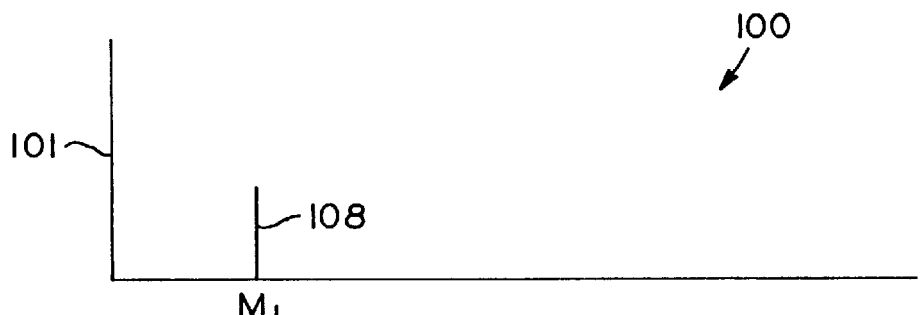
FIG_7A
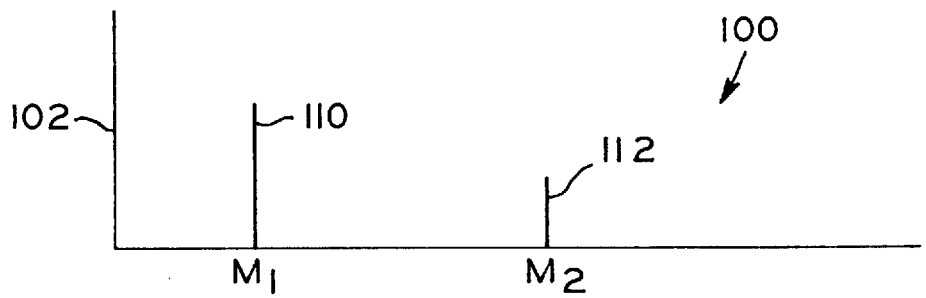
FIG_7B
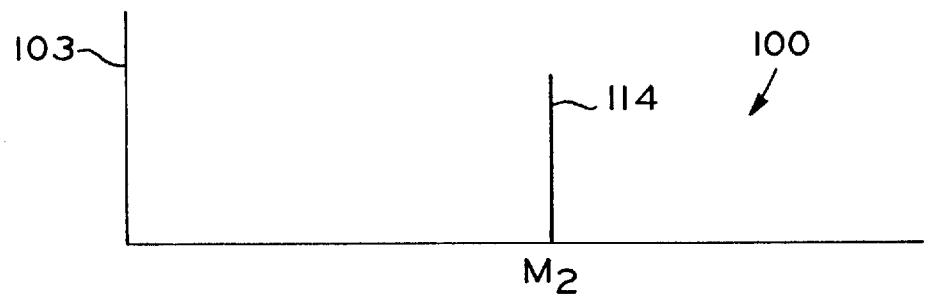
FIG_7C
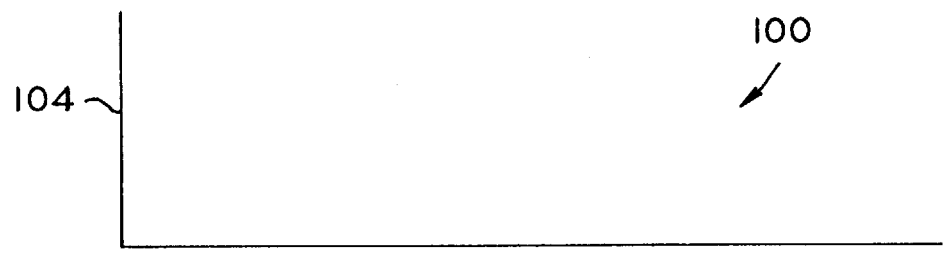
FIG_7D

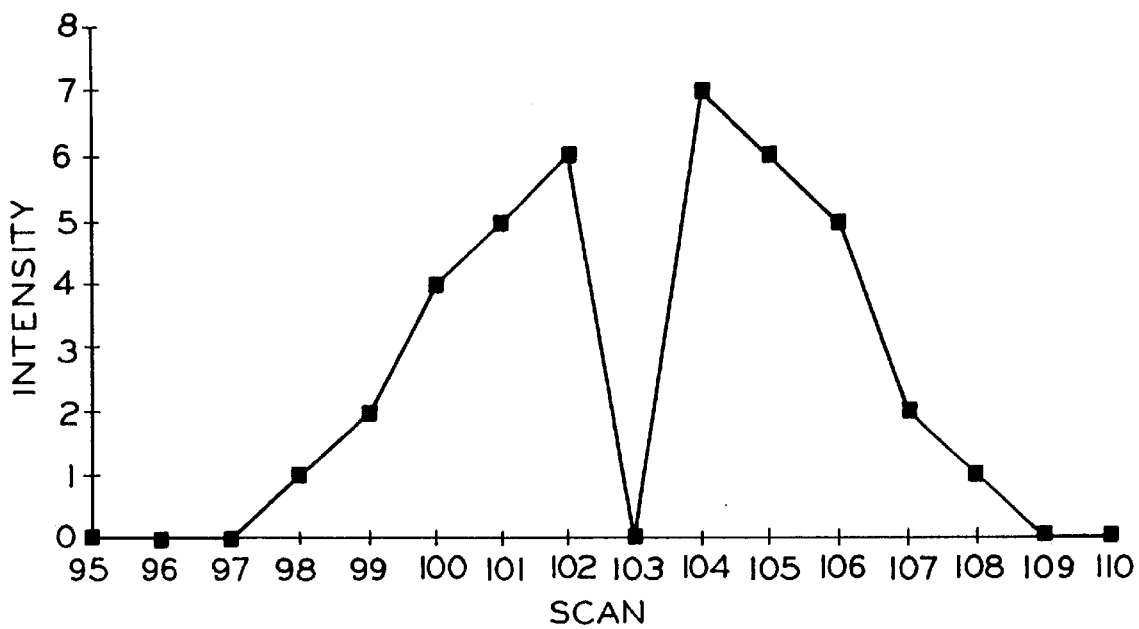
FIG_8
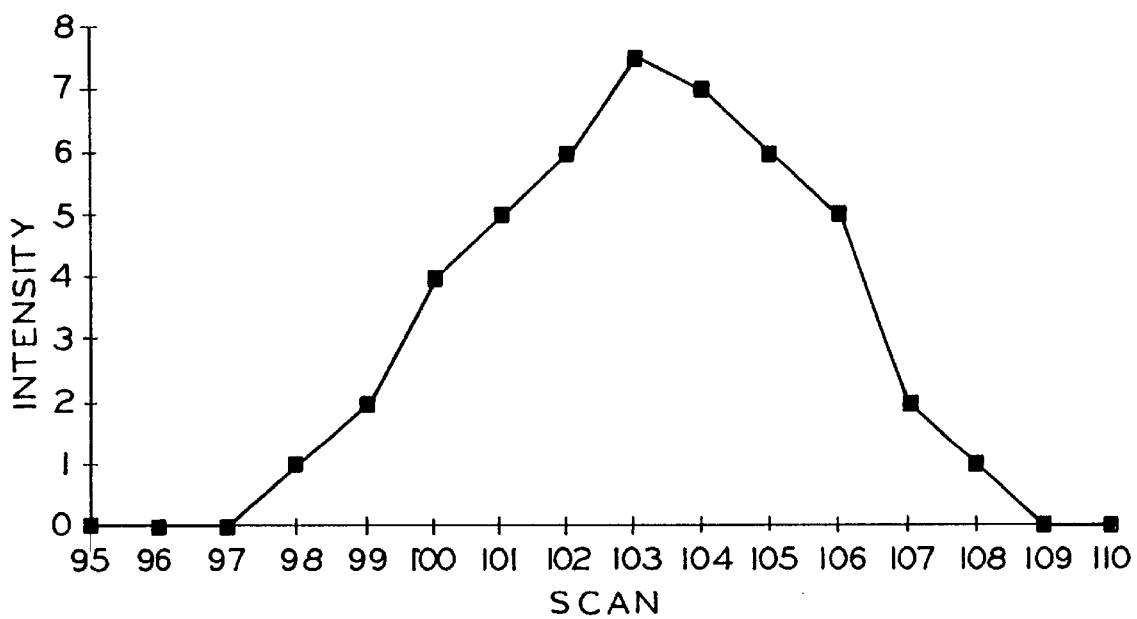
FIG_9

SYSTEM AND METHODS FOR QUALITATIVELY AND QUANTITATIVELY COMPARING COMPLEX ADMIXTURES USING SINGLE ION CHROMATOGRAMS DERIVED FROM SPECTROSCOPIC ANALYSIS OF SUCH ADMIXTURES

FIELD OF THE INVENTION

The present invention relates to systems and methods of comparing complex admixtures, such as admixtures of peptide digests resulting from enzymatic digestion of proteins, in which the mixtures are qualitatively and/or quantitatively compared using selective ion chromatograms derived from spectroscopic analysis of such admixtures. More specifically, the present invention relates to systems and methods of comparing proteins in which the proteins are digested to provide peptide digests, the digests are fractionated, the digests are subjected to mass spectroscopic analysis, and the proteins are then compared using selective ion chromatograms derived from the spectroscopic analysis.

BACKGROUND OF THE INVENTION

Proteins have a diverse range of physical properties and perform a wide range of biological functions, including enzymatic catalysis, transport and storage, mechanical functions, movement, protection, information processing, and the like. Although proteins are manufactured naturally by living organisms to carry out these functions, many proteins can now be manufactured in large quantities using biological engineering technologies. Manufactured proteins have become important commercial products for treating disease and illness in human being and animal patients. For example, the protein insulin is used for treating patients with diabetes. Other commercially important proteins include tissue plasminogenactivator (TPA), erythropoieton (EPO), human growth hormone (hGH), interleukin II, and the like.

All proteins are composed of a linear sequence of amino acid residues. The amino acid residues are linked together by peptide bonds occurring between the amino group of one amino acid and the carboxyl group of the preceding amino acid. Molecules which are composed of a sequence of amino acid residues, such as proteins, are known generally as peptides. Proteins are a class of peptides referred to as polypeptides and typically comprise a sequence of fifty or more amino acid residues. As such, proteins are extremely large biological molecules having molecular weights typically exceeding 5000 amu. For example, insulin is characterized by a sequence of 51 amino acid residues and a molecular weight of 5808 daltons. As another example, human growth hormone is characterized by a sequence of 191 amino acids and a molecular weight of 22,125 daltons.

Each kind of protein has a unique sequence of amino acids. Additionally, the relative abundances of the various kinds of amino acid residues in a protein also tends to be unique. As such, the amino acid sequence and relative abundances of the amino acid residues are fingerprints of a protein molecule. Generally, the function or functions of a protein are often extremely dependent upon such fingerprint characteristics. Even minor changes in such characteristics may destroy the function or functions of a protein molecule. Examples of possibly deleterious changes include omission of an amino acid residue in a sequence, inclusion of an extra amino acid residue in sequence, a change in the amino acid order of a sequence, substitution of an incorrect amino acid residue in place of the desired amino acid residue, undesirable oxidation of one or more functional groups of one or more amino acid residues, N-terminal modifications, unintended addition, deletion, or modification of side chains, unintended cleavage, unintended hydroxylation, and the like.

Accordingly, when studying, developing, or manufacturing protein products, it is critical that the protein product under consideration is being, or has been, manufactured correctly and consistently. It is essential, therefore, to be able to qualitatively and quantitatively compare production material to product standards. Because of the enormous size of protein molecules, however, it is not practical to work with an entire protein molecule when performing such qualitative and/or quantitative analysis. Accordingly, it is desirable to first cleave a protein into smaller, more manageable pieces by hydrolysis of the peptide bonds between one or more amino acid residues. The result of such hydrolysis is an admixture comprising one or more peptides and/or one or more individual amino acids, depending upon the hydrolysis conditions that were used.

Proteins can be cleaved into smaller pieces using a variety of techniques, including chemical and enzymatic digestion. Enzymatic digestion is one of the most frequently used techniques for cleaving a protein molecule into smaller, more manageable pieces, because some specific enzymes tend to cleave a protein molecule at extremely specific cleavage sites. For example, the enzyme trypsin cleaves a protein molecule only on the carboxyl side of the amino acid residues of lysine (abbreviation K) and arginine (abbreviation R). As another example, the enzyme chymotrypsin cleaves protein molecules on the carboxyl side of the aromatic amino acid residues phenylalanine, tyrosine, and tryptophan. Theoretically, digestion of two identical protein molecules by the same enzyme activity should yield two identical admixtures of peptide digests. Techniques for carrying out enzymatic digestion are widely known in the art and are generally described in G. Allen, Laboratory Techniques in Biochemistry and Molecular Biology (R. H. Burdon and P. H. Knippenburg; eds.) Vol. 9, Sequencing of Proteins and Peptides, Elsevier Press, 1989.

Unfortunately, even if a protein is cleaved into smaller, more manageable pieces, comparing the resultant pieces of one protein molecule to those of another protein molecule is still a challenging problem. The problem is particularly vexing for qualifying commercial production material in which comparison between production material and product standards is desirably accomplished relatively quickly, because many of the previously known methods for characterizing a protein sufficiently to allow meaningful comparisons to be made are too expensive, too time consuming, too inaccurate, and/or yield too little information about the protein. Meaningful and practical comparisons between production material and product standards has remained on the wish list of the industry for a long time. Accordingly, methods allowing fast, accurate, repeatable, informative, and economical comparisons of protein molecules are needed.

SUMMARY OF THE INVENTION

Significantly, the present invention allows comprehensive qualitative and quantitative comparisons between two or more complex mixtures to be rapidly and automatically made using spectroscopic data generated from the mixtures to be compared. The present invention provides an approach which is fast, accurate, reliable, and repeatable.

The present invention may be used to compare an incredibly wide variety of mixtures, including mixtures of manmade and/or natural products. Such mixtures may be organic, inorganic, solid, gaseous, liquid, or combinations thereof. So long as the mixture can be subjected to spectroscopic analysis, the present invention may be used. However, due to the ability of the present invention to easily compare complex mixtures, the present invention is particularly suitable for studying complex admixtures obtained from biological materials, such as proteins, blood, tissue, cultures, and the like. For example, biological screening areas could use the present invention to identify chemical differences between mixtures that might relate to differences in activity. With respect to proteins in particular, the quantitative information provided by the invention would be useful during protein development and/or manufacturing to qualitatively and quantitatively analyze structurally complex protein products.

Advantageously, the present invention is capable of comparing spectroscopic data of complex mixtures, wherein the spectroscopic data is obtained from any of a wide variety of spectroscopic approaches. Representative examples of spectroscopic approaches suitable in the practice of the present invention would include, but not be limited to, mass spectroscopy, ultraviolet spectroscopy, infrared spectroscopy, atomic spectroscopy, NMR spectroscopy, raman spectroscopy, emission spectroscopy, and the like. The present invention, however, is particularly suitable for comparing mass spectroscopic data obtained from chromatographically fractioned mixtures. Due to the vast quantities of data generated by mass spectroscopic analysis, manual or visual comparisons of data is not practical, or even reliable. The present invention provides an automated way of carrying out rapid, accurate, qualitative or quantitative comparisons between the mass spectroscopic data for two or more samples.

In one aspect, the advantages of the present invention are achieved by a system for analyzing a protein sample. The system includes a reactor vessel, a chromatographic column, a mass spectrometer, and a computer system. The reactor vessel comprises an enzyme activity capable of digesting the protein sample in order to provide a plurality of peptide digests, an inlet port for receiving the protein to be digested, and an exit port for discharging the peptide digests. The chromatographic column comprises a chromatographic medium capable of chromatographically fractionating the peptide digests as the peptide digests are eluted through the column, wherein the chromatographic column comprises an inlet port for receiving the peptide digests, said inlet port being in flow communication with the exit port of the reactor vessel, and wherein the chromatographic column comprises an exit port for discharging an effluent comprising the chromatographically fractionated peptide digests. The mass spectrometer is capable of generating a mass spectroscopic data set comprising data from which a first plurality of selective ion chromatograms for the fractionated peptide digests can be generated. The mass spectrometer has an inlet port for receiving the chromatographically fractionated peptide digests. The inlet port is in flow communication with the exit port of the chromatographic column. The computer system is operationally coupled to the mass spectrometer such that the computer system is capable of analyzing the mass spectroscopic data set. The computer system comprises programming comprising:

(i) instructions enabling the computer system to compute a plurality of selective ion chromatograms, wherein the selective ion chromatograms are derived from the mass spectroscopic data set;

(ii) instructions enabling the computer system to compute a plurality of peak areas of the selective ion chromatograms; and (iii) instructions enabling the computer to calculate at least one value indicative of the relative abundance of at least one of the peptide digests, wherein the relative abundance value is derived from information comprising at least two peak areas selected from a peak area of an intended form of a peptide digest, a peak area of a first variant of said intended form of a peptide digest, a peak area of a second variant of said intended form of a peptide digest, and a peak area of a reference peptide digest.

In another aspect, the present invention relates to a system for comparing a first protein sample to a second protein sample. The system includes a reactor vessel, a chromatographic column, a mass spectrometer, and a computer system. The reactor vessel comprises an enzyme activity capable of digesting each protein sample in order to provide a plurality of peptide digests corresponding to each of the samples, an inlet port for receiving the protein sample to be digested, and an exit port for discharging the corresponding peptide digests. The chromatographic column comprises a chromatographic medium capable of chromatographically fractionating the peptide digests resulting from the digestion of each protein sample The chromatographic column comprises an inlet port for receiving the peptide digests, and the inlet port is in flow communication with the exit port of the reactor vessel. The chromatographic column also comprises an exit port for discharging an effluent comprising the chromatographically fractionated peptide digests. The mass spectrometer is capable of generating a mass spectroscopic data set comprising data from which plurality of selective ion chromatograms for each plurality of the fractionated peptide digests can be generated. The mass spectrometer has an inlet port for receiving the chromatographically fractionated peptide digests, and the inlet port is in flow communication with the exit port of the chromatographic column. The computer system is operationally coupled to the mass spectrometer such that the computer system is capable of analyzing the mass spectroscopic data set generated for each plurality of peptide digests. The computer system comprises programming comprising:

(i) instructions enabling the computer system to compute a first plurality of selective ion chromatograms corresponding to the plurality of digests of the first protein sample and a second plurality of selective ion chromatograms corresponding to the plurality of digests of the second protein sample, wherein the first plurality of selective ion chromatograms is derived from the mass spectroscopic data set generated for the peptide digests of the first protein sample, and the second plurality of selective ion chromatograms is derived from the mass spectroscopic data set generated for the peptide digests of the second protein sample;

(ii) peak picking instructions enabling the computer system to automatically locate chromatographic peaks of the first and second pluralities of selective ion chromatograms;

(iii) instructions enabling the computer system to automatically match peaks between the first and second pluralities of selective ion chromatograms in order to identify matching peak pairs of the first and second pluralities of selective ion chromatograms; and (iv) instructions enabling the computer system to output results of said peak matching.

In another aspect, the present invention provides a method of comparing a protein sample to a reference protein. The method comprises the steps of:

(a) providing a predefined list of a plurality of peptides resulting from digestion of the reference protein by an enzyme activity, wherein said predefined list comprises at least two peptide digests selected from an intended form of a peptide digest, a first variant of said intended form of a peptide digest, a second variant of said intended form of a peptide digest, and a reference peptide digest, and wherein each of said peptides is characterized by a mass interval and a retention time interval for which each peptide is expected to be detected by a mass spectrometer;

(b) characterizing the reference protein sufficiently such that the relative abundance of one or more of said plurality of peptides relative to one or more other peptides of the reference protein can be determined;

(c) digesting the protein sample into a plurality of peptides using the enzyme activity;

(d) fractionating the plurality of peptides resulting from digestion of the protein sample;

(e) subjecting the fractionated peptides to mass spectroscopic analysis using a mass spectrometer in order to provide a mass spectroscopic data set from which a plurality of selective ion chromatograms for the fractionated peptide digests can be computed;

(f) computing a plurality of selective ion chromatograms wherein the selective ion chromatograms are derived from the mass spectroscopic data set and wherein each of the selective ion chromatograms is computed for a mass interval corresponding to a mass interval of one of the plurality of listed peptides resulting from digestion of the reference protein;

(g) calculating a plurality of peak areas of the selective ion chromatograms, wherein each peak area is calculated over a retention time interval corresponding to a retention time interval of one of the plurality of listed peptides resulting from digestion of the reference protein;

(h) calculating a value indicative of the relative abundance of at least one fractionated peptide to the extent such fractionated peptide is detected by the mass spectrometer, wherein said relative abundance value is derived from information comprising a plurality of said peak areas of the selective ion chromatograms; and (i) comparing said value of said at least one peptide to the corresponding relative abundance value of the corresponding at least one peptide of the reference protein.

In another aspect of the present invention, the present invention provides a method of comparing a first protein sample to a second protein sample. The method comprises the steps of:

(a) digesting the first protein sample into a first plurality of peptides using an enzyme activity;

(b) digesting the second protein sample into a second plurality of peptides using the enzyme activity;

(c) fractionating each of the first and second pluralities of peptides;

(d) subjecting each of the first and second fractionated pluralities of peptides to mass spectroscopic analysis in order to generate a mass spectroscopic data set for each plurality of fractionated peptides from which a plurality of selective ion chromatograms for each plurality of fractionated peptides can be computed;

(e) computing a first plurality of selective ion chromatograms for the first plurality of fractionated peptides, wherein the first plurality of selective ion chromatograms is derived from the mass spectroscopic data set generated for the first plurality of fractionated peptides;

(f) computing a second plurality of selective ion chromatograms for the second plurality of fractionated peptides, wherein the second plurality of selective ion chromatograms is derived from the mass spectroscopic data set generated for the second plurality of fractionated peptides;

(g) automatically locating chromatographic peaks of the first and second pluralities of selective ion chromatograms;

(h) automatically matching peaks between the first and second pluralities of selective ion chromatograms in order to identify matching peak pairs; and (i) outputting information indicating results of said peak matching.

BRIEF DESCRIPTION OF THE DRAWINGS

The above-mentioned and other features and advantages of this invention, and the manner of attaining them, will become more apparent, and the invention will be better understood, with reference to the following description of preferred embodiments of the invention taken in conjunction with the accompanying drawings, wherein:

FIG. 1 is a schematic representation of a digestion reaction in which a reference protein sample is enzymatically digested by an enzyme activity;

FIG. 2 is a schematic representation of a digestion reaction in which a protein sample is enzymatically digested by an enzyme activity, wherein the peptide components of a portion of the protein molecules of the protein sample incorporate unintended modifications;

FIG. 3 is a schematic representation of a three dimensional plot of an HPLC mass spectroscopic data set;

FIG. 4 is a representation of a selective ion chromatogram having one chromatographic peak;

FIG. 5 is a selective ion chromatograph containing two chromatographic peaks;

FIG. 6 shows a system used for analyzing protein samples in accordance with the practices of the present invention;

FIGS. 7a, 7b, 7c, and 7d are schematic representations of four consecutive scans acquired from the mass spectroscopic analysis of the peptide digests obtained from enzymatic digestion of a protein;

FIG. 8 is a selective ion chromatogram computed for a mass interval having a drop out caused by fragments oscillating around the mass boundary of the selective ion chromatogram; and FIG. 9 shows the same selective ion chromatograph of FIG. 6 recomputed using the peak grouping technique of the present invention to eliminate the drop out.

The exemplifications set out herein illustrates preferred embodiments of the invention, and such exemplification is not to be construed as limiting the scope of the invention in any manner.

DETAILED DESCRIPTION OF THE PREFERRED EMBODIMENTS

The present invention will now be described with reference to the various representative aspects of the invention depicted in FIGS. 1 through 9. However, the aspects of the present invention disclosed below are not intended to be exhaustive or to limit the invention to the precise forms disclosed in the following detailed description.

FIG. 1 is a schematic illustration of a representative digestion reaction in which a protein sample 1 is enzymatically digested by an enzyme activity. Protein sample 1 of FIG. 1 represents a reference protein whose amino acid sequence has been sufficiently characterized such that the form and identity of all peptide digests resulting from the digestion are easily determined from the known amino acid sequence of the sample. For purposes of illustration, the enzyme activity of FIG. 1 is the enzyme trypsin, and protein sample 1 comprises one or more cleavage sites 2 at which the protein sample 1 would be cleaved as a result of digestion by trypsin. Cleavage sites 2 of the protein sample 1 are generally designated as R in the case of arginine, and K in the case of lysine. Digestion of protein sample 1 by trypsin yields a plurality of peptide digests 3, 4, 5, 6, and 7, respectively. In the reaction exemplified in FIG. 1, only five such peptide digests are shown resulting from the tryptic digestion of protein sample 1. However, the number of such digests would vary in actual practice depending upon the nature of the protein being digested, the digestion conditions, the particular enzyme activity being used to digest the protein, and the like.

Although trypsin is the enzyme activity represented in FIG. 1, the activity used in the practice of the present invention to cleave a protein sample into smaller, more manageable pieces may be any enzyme or chemical activity known in the art which is capable of repeatedly and accurately cleaving a protein at particular cleavage sites during digestion. Suitable activities are widely known and a suitable activity may be selected using conventional practices. Examples of such enzyme or chemical activities would include, as representative examples, the enzyme trypsin which hydrolyzes peptide bonds on the carboxyl side of lysine and arginine, the enzyme chymotrypsin which hydrolyzes peptide bonds on the carboxyl side of aromatic residues (phenylalanine, tyrosine, and tryptophan), and cyanogen bromide (CNBr) which chemically cleaves proteins at methionine residues. The enzyme trypsin is often a preferred enzyme activity for cleaving proteins into smaller, more manageable pieces, because trypsin is characterized by low cost and highly reproducible and accurate cleavage sites at the amino acids arginine and lysine occurring in the amino acid sequence of protein molecules.

It is often desirable to manufacture a protein product which is intended to be substantially identical to a reference protein such as the reference protein sample 1 of FIG. 1, or which is intended to comply with product specifications corresponding to the protein product. However, the resultant protein product may tend to differ from the reference protein or from the pertinent product specification. Additionally, various protein molecules constituting the protein product may even tend to differ from each other as well. Such differences arise because one or more of the peptide components of the various protein molecules constituting the production material may tend to undergo unintended modifications during or after production.

For example, FIG. 2 is a schematic representation of the tryptic digestion of a protein sample 1' intended to correspond in structure to reference protein sample 1 of FIG. 1. Like protein sample 1 of FIG. 1, protein molecules 1a', 1b', and 1c' constituting protein sample 1' comprise cleavage sites 2' generally designated R in the case of arginine and K in the case of lysine, and digestion of protein sample 1' yields peptide digests 3', 4', 5', 6a', 6b', 6c', and 7'. However, during or after production, one of the peptide components of the protein sample 1' underwent two different, unintended modifications such that three different forms of protein molecules 1a', 1b', and 1c' actually constitute protein sample 1'. Unintended modifications of the protein are shown schematically as the substitute X on protein molecule 1b' and as Y on protein molecule 1c'. Peptide digest 6a' (FIG. 2) represents the intended form of the peptide digest corresponding to the peptide digest 6 (FIG. 1), whereas peptide digests 6b' and 6c', bearing the modifications X and Y, respectively, represent unintended forms, or variants, of that peptide digest.

For purposes of illustration, only the one peptide digest 6a' is shown as having modified variants 6b' and 6c' in the population of protein molecules 1a', 1b', and 1c' constituting protein sample 1'. In actual practice, however, one or more other peptide digests may be present in one or more unintended, modified forms, or variants, as well. Further, although only three different protein molecules 1a', 1b', and 1c' are shown in FIG. 2, a population of protein molecules constituting a protein sample may include more than three different forms of protein molecules, particularly if many of the peptide components of the protein sample undergo modification during or after synthesis.

If the relative abundance of peptide digest variants 6b' or 6c', or any other variant of any of the intended peptide digests, is too high, or perhaps too low if the presence of some of the variant is desired, the efficacy of the protein product may suffer or even be destroyed. Product specifications for a protein product, therefore, may establish upper and/or lower limits for the relative abundance of particular peptide digest variants which may be present in order for a protein sample to comply with the corresponding protein product specification. For example, according to a representative approach, a product specification might recite that the tryptic digests of protein sample 1' could include up to Z parts by weight of peptide digest 6b' and up to N parts by weight of peptide digest 6c' based upon 100 parts by weight of peptide digest 6a', wherein Z and N would represent maximum amounts of digests 6b' and 6c' that could be present without adversely affecting the efficacy of protein sample 1'. In such circumstances, the relative abundances of peptide digests 6a', 6b', and/or 6c' are determined relative to each other.

According to another representative approach, one or more of the other peptide digests 3', 4', 5', and/or 7' may be sufficiently stable such that no substantial amounts of unintended, modified variants of such peptides exist. Under such circumstances, such one or more digests can serve as a reference from which the relative abundance of other digests can be determined. Product specifications may, then, establish upper and/or lower limits for the abundance of particular peptide digest variants which may be present relative to the amount of the reference digest or digests. For example, if peptide digest 3' were to qualify as a reference digest, product specifications could recite that the tryptic digests of protein sample 1' could include up to Z parts by weight of peptide digest 6b' and up to N parts by weight of peptide digest 6c' based upon 100 parts by weight of peptide digest 3', wherein Z and N in this scenario would represent maximum amounts of digests 6b' and 6c' that could be present without adversely affecting the efficacy of protein sample 1'.

For purposes of quality control, therefore, it is important to monitor the relative abundance of one or more peptide digests of interest, and/or variants thereof, in order to ensure that the protein product being manufactured consistently meets product specifications or to ensure that the protein product is sufficiently identical to the corresponding reference protein. In the case of a reference protein, such as protein sample 1 of FIG. 1, the form, identity, and relative abundances of all peptide digests resulting from tryptic digestion are easily determined by inspection and/or calculation from the known amino acid sequence of the sample. However, in the case of a protein sample obtained from lab or manufacturing scale production, the relative abundance of the various peptide digests resulting from enzymatic digestion cannot be so easily calculated in the same manner without first undertaking time consuming analytical testing of the various protein molecules constituting the sample in order to determine the amino-acid sequence of each such molecule. Of course, this kind of laborious approach is not practical for monitoring the quality of production material. A different approach is needed to compute such relative abundance values.

Advantageously, in one embodiment, the present invention uses peak areas of mass spectroscopic, selective ion chromatograms generated from the peptide digests of a protein sample in order to derive the relative abundance of one or more of such peptide digests. The mass-spectroscopically derived relative abundance of such peptide digest or digests may then be compared to the relative abundance of the peptide digests in the pertinent reference protein, or to the relative abundance of the peptide digests in another protein sample other than a reference protein, or to the relative abundance of peptide digests in both the reference protein and other protein samples, or to the ranges recited in a corresponding specification, or the like. Differences and similarities between two or more proteins, or between a protein and a specification, may thereby be easily determined with respect to the constituent peptide content of such proteins. This approach is fast, accurate, and repeatable.

The selective ion chromatograms of the type used in the practice of the present invention will now be further described with respect to FIGS. 3 through 5. FIG. 3 is a schematic representation of a three-dimensional data set 10 acquired by mass spectroscopic analysis of a complex mixture comprising a plurality of mass spectroscopically resolvable species, such as the chromatographically-fractionated, enzymatic peptide digests of a protein sample. Axis 12 represents the ion current response range for the species which were subjected to spectroscopic analysis. Axis 14 represents the time range over which mass spectroscopic data was collected. Axis 16 represents the range of mass-to-charge ("m/z") ratios over which data was collected. Chromatographic peaks 18 and 21 represent the chromatographic response of species subjected to chromatographic analysis. Although such peaks are shown as vertical lines in FIG. 3, in actuality, such peaks would be three dimensional volumes extending upward over particular time and m/z ranges. As used in the practice of the present invention, a selective ion chromatogram refers to a plot of ion current response versus time for a particular m/z interval, or "mass interval" as such intervals are often called, of the data set. A representative selective ion chromatogram computed for the m/z interval of $m/z_i$ is designated generally as 20 in FIG. 3 and includes a peak 21.

Selective ion chromatogram 20 of FIG. 3 is shown in more detail in FIG. 4. There, selective ion chromatogram 20 is computed relative to axis 22 representative of ion current response and axis 24 representative of the time period over which data for the mass interval $m/z_i$ was collected. Selective ion chromatogram 20 includes the peak 21 occurring within a retention time interval extending from $t_1$ to $t_2$. The retention time interval from $t_1$ to $t_2$ indicates the time period during which a species characterized by a m/z ratio in the interval $m/z_i$ was detected by the mass spectrometer. Peak 21 has a peak area represented by the shaded area.

Such peak area is directly proportional to the abundance of the species which are characterized by a m/z ratio in the mass interval $m/z_i$ and which eluted in the $t_1$ to $t_2$ retention time interval. Ratios of such peak areas may be easily computed and compared. Thus, ratios of the peak areas of selective ion chromatograms may be used to calculate the amount of any eluting species or combination of species relative to any other eluting species or combination of species, as desired.

For example, if protein sample 1' of FIG. 2 were to be enzymatically digested to provide peptide digests 3', 4', 5', 6a', 6b', 6c', and 7', and if such digests were to be preferably fractionated and then subjected to mass spectocopic analysis to yield a mass spectroscopic data set from which selective ion chromatograms for the peptide digests could be computed, the abundance of each of peptide digests 6a', 6b', or 6c', for example, relative to the total amount of peptide digests 6a', 6b', and 6c' could be given by the following expressions, respectively:

$$r_a = \frac{A_{6a}}{[A_{6a} + A_{6b} + A_{6c}]}$$

$$r_b = \frac{A_{6b}}{[A_{6a} + A_{6b} + A_{6c}]}$$

$$r_c = \frac{A_{6c}}{[A_{6a} + A_{6b} + A_{6c}]}$$

wherein $r_a$, $r_b$, and $r_c$ represent the relative abundances of each of peptide digests $6_a'$, $6_b'$, and $6_c$, respectively, relative to the total amount of such peptide digests, and $A_{6C}$, $A_{6b}$, and $A_{6c}$ represent selective ion chromatographic peak areas corresponding to peptide digests $6_a'$, $6_b'$, and $6_c$, respectively. Similarly, the abundance of peptide digests 6a', 6b', or 6c' relative to the amount of reference peptide digest 3' could be given by the following expressions, respectively:

$$r_a' = \frac{A_{6a}}{A_3}$$

$$r_b' = \frac{A_{6b}}{A_3}$$

$$r_c' = \frac{A_{6c}}{A_3}$$

wherein $r_a$, $r_b$, and $r_c$ represent the relative abundances of each of peptide digests $6_a'$, $6_b'$, and $6_c$, respectively, relative to peptide digest 3', $A_{6C}$, $A_{6b}$, and $A_{6c}$ are as defined above, and $A_3$ is the selective ion chromatographic peak area corresponding to peptide digest 3'.

The expressions denoted above for calculating the relative abundance of peptide digests $6_a'$, $6_b'$, and $6_c$, are intended to be illustrative and are not presented or intended to limit the present invention to the use of only these particular expressions. For any particular protein, a variety of values can be defined which would characterize the protein in a meaningful way. The precise values defined would vary from protein to protein and would depend upon a variety of factors including the nature of the protein itself, the desired activity under investigation, the nature of the peptide digests, the enzyme activity being used, and the like.

Another selective ion chromatogram 20 is shown in FIG. 5. Selective ion chromatogram 20 of FIG. 5 is identical to selective ion chromatogram of FIG. 4, except that selective ion chromatogram 20 includes a second peak 26 in the retention time interval extending from $t_3$ to $t_4$. The probability of two or more peptide digests having the same m/z ratio is low, but can still occur as is shown in FIG. 5. However, the probability of two peptide digests having the same m/z ratio, but which generate a peak in the same or overlapping retention time intervals is extremely low. Accordingly, in the practice of the present invention, it is preferably assumed when working with peak areas of selective ion chromatograms that each peak area of a selective ion chromatogram is associated with a respective one peptide digest.

Because the relative abundance of peptide digests can be so easily derived from selective ion chromatograms computed for the peptide digests, peak areas from the selective ion chromatograms of the peptide digests of a protein sample offer a facile way to qualitatively and quantitatively compare a protein sample to other protein samples or to a reference protein, as desired. For example, to quantitatively compare a protein sample to a reference protein, or to a product specification, or to another protein sample, the protein samples under consideration would first be digested to provide a plurality of peptide digests. If the protein sample is to be compared to a reference protein, the protein sample would be digested using the same activity which was used to define the cleavage sites of the reference protein molecule 1. In the present example under discussion, the enzyme trypsin was used to determine the cleavage sites of the reference protein molecule 1. Accordingly, trypsin would be used to digest the protein sample being compared to the reference protein molecule 1. In an analogous fashion, if two protein samples are to be compared, both samples should be digested using the same activity. If the protein sample is to be compared to a specification, the same activity should be used for digestion as was used to establish the specification. The resultant digests would then preferably be fractionated and subjected to mass spectroscopic analysis to generate a mass spectroscopic data set. Selective ion chromatograms could then be computed from the data set. One or more values indicative of the relative abundance of the peptide digest or digests of interest then could be derived from the peak areas of selective ion chromatograms corresponding to the respective digests. These relative values could then be compared to corresponding values determined for a reference protein, or to value ranges recited in a product specification, or to values derived for another protein sample, as desired.

FIG. 6 shows a particularly preferred system 30 suitable in the practice of the present invention for generating selective ion chromatograms from the peptide digests of a protein sample under consideration. System 30 includes a reactor vessel 32 comprising an activity which is capable of enzymatically or chemically digesting the protein sample. In the preferred embodiment of FIG. 6, reactor vessel 32 is an on-line enzyme digestion column having inlet port 34 for receiving the protein sample and exit port 36 for discharging the resulting peptide digests. However, the reactor vessel could be any suitable container in which the digestion reaction could be carried out. Inlet port 34 and exit port 36 are in fluid communication with an internal reaction chamber 37 of the reactor vessel 32. Preferably, the on-line enzyme digestion column used as the reactor vessel 32 is of the type in which the enzyme activity is immobilized on a suitable immobilizing medium housed in the internal reaction chamber 37 of the column. On-line enzyme digestion columns suitable for use as reactor vessel 32 are commercially available. A specific example of one such on-line digestion column found to be suitable in the practice of the present invention is commercially available as the Porozyme™ Immobilized Trypsin Cartridge from Perspective Biosystems, Framingham, MA.

Exit port 36 of reactor vessel 32 is connected to on-line chromatographic column 38 by pathways 39 and 40. Pathways 39 and 40 are coupled by switching member 42. Chromatographic column 38 includes a chromatographic medium which, in cooperation with a suitable solvent system, is capable of chromatographically fractionating peptide digests received from reactor vessel 32. Chromatographic column 38 includes an inlet port 44 for receiving the peptide digests and an exit port 46 for discharging an effluent comprising the chromatographically fractionated peptide digests.

In a preferred embodiment, chromatographic column 38 is a reverse-phase HPLC analytical column comprising a fractionating medium capable of fractionating the peptide digests when the digests are eluted through chromatographic column 38 using reverse phase HPLC techniques. In order to practice such techniques, it is preferred that the chromatographic medium is hydrophobic because the peptide digests themselves tend to by hydrophobic in nature. Such columns suitable in the practice of the present invention are widely known. A specific example of one HPLC analytical column found to be suitable in the practice of the present invention is commercially available as the Vydac™ C-18 HPLC column from the Separations Group, Hesperia, Calif.

Exit port 46 of chromatographic column 38 is connected to mass spectrometer 48 by pathways 49 and 50 through switching member 52. Mass spectrometer 48 may be any mass spectroscopic instrument capable of generating a mass spectroscopic data set from which selective ion chromatograms for the peptide digests can be generated. In preferred embodiments, the mass spectrometer 48 is a quadropole electrospray ionization mass spectrometer. A specific example of one such quadropole electrospray ionization mass spectrometer found to be suitable in the practice of the present invention is commercially available as the Finnegan SSQ 710C single stage quadruple mass spectrometer with electrospray source from Finnegan MAT, San Jose, Calif.

Computer system 54 is operatively coupled to mass spectrometer 48 by a suitable interface schematically represented as interface 56 in FIG. 6. Computer system 54 includes hardware and software components which enable computer system 54 to analyze the mass spectroscopic data set generated by mass spectrometer 48. In particular, computer system 54 comprises instructions which enable computer system 54 to compute selective ion chromatograms from the mass spectroscopic data and to derive values indicative of the relative abundance of the peptide digest or digests under consideration from such selective ion chromatograms. Further details of the instructions will be discussed below where a preferred mode of operation of system 30 is explained.

System 30 includes containers for holding the various solvents used during the operation of system 30. The number and nature of such containers and corresponding solvents will vary depending upon the particular mode of operation being used with respect to digestion, fractionation, and mass spectroscopic analysis. In a preferred mode of operation to be discussed below, system 30 uses four solvents retained in four solvent containers 58, 60, 62, and 64, respectively. Containers 58 and 60 retain the solvents used with respect to enzymatic digestion of the protein sample in reactor vessel 32. Container 58, for example, retains an enzyme activation buffer. When pumped through reactor vessel 32, the enzyme activation buffer activates the enzyme activity so that the enzyme activity will digest the protein sample as the protein sample is transported through reactor vessel 32. Container 60 retains a cleansing solvent used to wash reactor vessel 32 before and/or after a protein digestion in order to remove any left-over peptide digest and/or protein residue remaining in reactor vessel 32 from a previous run.

The particular solvents used as the activation buffer and the cleansing solvent are not particularly critical and will vary depending upon the nature of the protein sample, the enzyme activity, and the like. Suitable solvents for any particular digestion operation may be selected in accordance with conventional practices. Often, if the reactor vessel is obtained commercially, the vendor and/or manufacturer may supply the identity of suitable solvents. As one specific example of solvents suitable for use as the activation buffer and the cleansing solvent when the commercially available porozyme trypsin column identified above is used as reactor vessel 32, a buffer solution of containing 50 mM Tris-C1 and 10 mM calcium chloride and characterized by a pH of 8.2 is suitable as the activation buffer, and acetonitrile is suitable as the cleansing solvent.

Containers 62 and 64 retain the solvents used to carry out reverse phase HPLC fractionation of the peptide digests as the digests are transported through chromatographic column 38. The particular solvents used to carry out such reverse phase fractionation are not critical, and suitable solvents could be selected in accordance with conventional practices. Generally, as known in the art, one of the solvents will tend to be relatively hydrophilic, and the other solvent will tend to be relatively hydrophobic. As a specific example of a solvent combination found to be suitable in the practice of the present invention, the hydrophilic solvent retained in container 62 may be water including an effective amount, e.g., about 0.1% by weight, of trifluoroacetic acid (TFA), and the hydrophobic solvent retained in container 64 may be a solution comprising 99.9 parts by weight of acetonitrile (ACN) and 0.1 parts by weight of TFA.

Solvent containers 58, 60, 62, and 64 are connected by pathways 66, 67, 68, and 69, respectively, to pump 70, which in a preferred embodiment is an HPLC pump capable of pumping solvents, either singly or in any combination, at any desired independent flow rate or rates from containers 58, 60, 62, and 64. Pump 70 is connected to autosampler 72 by pathway 74. Protein samples are introduced into system 30 through autosampler 72. Autosampler 72 is connected to reactor vessel 32 by pathways 76 and 78 through switching member 80. By-pass pathway 82 extends from switching member 80 to switching member 42.

Switching members 42, 52, and 80 help control flow of materials through system 30. For example, switching member 80 can be set so that materials emerging from autosampler 72 may be transported from pathway 76 to reactor vessel 32 through pathway 70 or to chromatographic column 38 through pathways 82 and 40, thus by-passing reactor vessel 32. Similarly, switching member 42 can be set so that materials can be transported from pathway 39 or pathway 82, as the case may be, to chromatographic column 38 via pathway 40 or to waste container 84 via pathway 86, as desired. Additionally, switching member 52 can be set so that materials emerging from chromatographic column 38 may be transported from pathway 49 either to mass spectrometer 48 through pathway 50 or to waste container 88 through pathway 90, as desired.

According to a preferred mode of operation of system 30, reactor vessel 32 and chromatographic column 38 initially may be regenerated and/or activated, if needed, in preparation for the operation. For example, to regenerate chromatographic column 38, column 38 may first be rinsed, if necessary, with 100% of the hydrophobic solvent of container 64 in order to wash away any peptide digest and protein residue remaining in the column 38 from a previous run. Column 38 is then rinsed with 100% of the hydrophilic solvent of container 62 such that any of the substantially hydrophobic peptide digests, subsequently entering column 38 from reactor vessel 32 will initially stick and be loaded on to the hydrophobic chromatographic medium of column 38 so that reverse phase fractionation of the peptides may be carried out. During such washing and rinsing, switching members 42, 52, and 80 are set so that one solvent or the other may be transported by pump 70 through column 38 and discharged to waste container 88 via pathways 68 or 69 (as appropriate), 74, 76, 82, 40, 49 and 90.

To regenerate and activate reactor vessel 32, reactor vessel 32 may first be rinsed, if necessary, with acetonitrile from container 60 in order to wash away any protein and/or peptide digest residue remaining in reactor vessel 32 from a previous run. Reactor vessel 32 is then activated with activation buffer from container 58. During such rinsing and activation, switching members 42 and 80 are set so that the acetonitrile or the activation buffer, as the case may be, are transported by pump 70 through reactor vessel 32 and discharged to waste container 84 via pathways 66 or 67 (as appropriate), 74, 76, 78, 39 and 86.

In further preparation for carrying out the preferred mode of operation of system 30, a protein sample under consideration is loaded into autosampler 72. The protein sample is typically loaded into the autosampler 72 at a suitable concentration in admixture with a suitable volume of a suitable solvent. The particular solvent, solvent volume, and sample concentration of the sample admixture may be selected in accordance with conventional practices. Examples of suitable solvents for the protein sample admixture include, for example, a buffered aqueous medium having a suitable pH, e.g., a pH in the range from 7.5 to 8.5.

Generally, a concentration of protein sample in the protein sample admixture and the volume of solvent in the admixture are selected so that the resultant peptide digests subsequently introduced to the mass spectrometer will be present in sufficient amounts to generate sufficient mass spectroscopic signals enabling meaningful mass spectroscopic analysis of the peptide digests to be carried out. If the amount of the protein sample in the admixture is too low, then the mass spectroscopic signals likewise may be at a level which is too low for meaningful analysis. On the other hand, if the amount of the protein sample in the admixture is too high, too much of the protein sample may remain undigested after transport through reactor vessel 32. A suitable concentration of protein sample in the admixture and a suitable volume of the solvent in the sample admixture can be determined experimentally in accordance with conventional practices. The selection of suitable concentrations and volumes will depend upon a variety of factors including the flow rate through the system, the solvent used in the admixture, the type of autosampler being used, the nature of the protein sample under consideration, the mass spectrometer being used, and the like. A concentration in the range from 0.25 mg/ml to 4 mg/ml, more preferably 2 mg/ml has been found to be suitable in the practice of the present invention.

With a protein sample admixture loaded in autosampler 72 and with reactor vessel 32 and chromatographic column 38 of system 30 readied for the initial phase of operation, switching member 80 is set so that activation buffer is pumped from container 58 to reactor vessel 32; switching member 42 is set so that the materials discharged from reactor vessel 32 are transported to chromatographic column 38; and switching member 52 is set so that effluent discharged from the chromatographic column is transported to waste container 88. Later, during a subsequent phase of the operation in which reverse phase fractionation of the peptide digests retained in the chromatographic medium of column 18 is carried out, switching member 80 will be set so that solvents by-pass reactor vessel 32, and switching member 52 will be set so that effluent discharged from column 38 is transported to mass spectrometer 48.

After switching members 42, 52, and 80 are appropriately set for the initial phase of the operation, a flow of activation buffer to reactor vessel 32 is established. Autosampler 72 then injects the protein sample admixture into the flow of activation buffer, and the protein sample is then transported by such flow to reactor vessel 32. The protein sample admixture and activation buffer enter reaction chamber 37 of reactor vessel 32 through inlet port 34. During the residence time in reaction chamber 37, the protein sample is digested into a plurality of peptide digests. The peptide digests, unreacted protein if any, and activation buffer are then discharged from reactor vessel 32 through exit port 36.

Generally, the activation buffer is transported through reactor vessel 32 at a suitable flow rate which provides a sufficient residence time in reactor vessel 32 such that substantially all of the protein sample will be digested by the enzyme activity. In embodiments of the present invention in which reactor vessel 32 is the Porozyme™ Immobilized Trypsin Cartridge having a 100 microliter reaction chamber volume as identified above and in which the sample admixture injected into the activation buffer flow comprises a concentration of about 3 mg/ml of protein sample, a flow rate of activation buffer of 25 microliters per minute, i.e., a residence time of four minutes, has been found to be suitable in the practice of the present invention.

In carrying out the protein digestion, the activation buffer and reactor vessel 32 are also maintained at a temperature in a suitable temperature range at which digestion of the protein sample by the enzyme activity will take place. Such temperature may be selected in accordance with conventional practices depending primarily upon the type of enzyme activity being used to carry out digestion. In embodiments of the invention in which the enzyme activity is trypsin, maintaining the activation buffer and reactor vessel 32 at a temperature in the range of 20° C. to 60° C., more preferably 37° C. has been found to be suitable in the practice of the present invention.

The materials discharged from reactor vessel 32, including the peptide digests, unreacted protein if any, and activation buffer, are then transported to chromatographic column 38. The materials enter column 38 through inlet port 34. The peptide digests tend to stick to the hydrophobic chromatographic medium of column 38 such that an effluent comprising activation buffer, but substantially no peptide digests, is discharged from exit port 36 to waste container 88. After substantially all of the peptide digests have been discharged from reactor vessel 32 and loaded onto chromatographic column 38, the setting of switching member 80 is changed so that solvent being pumped by pump 70 by-passes reactor vessel 32 and flows to chromatographic column 38 along by-pass pathway 82. The setting of switching member 52 is changed so that effluent discharged from chromatographic column 38 is transported to mass spectrometer 48. At substantially this time, pump 70 stops pumping activation buffer from container 58 and starts to pump hydrophilic chromatographic solvent from container 62 instead. As long as the flow of solvent through column 18 is 100% of the hydrophilic chromatographic solvent, substantially all of the peptide digests remain retained on the column, because substantially none of the digests would be soluble in 100% hydrophilic chromatographic solvent.

After flow of 100% hydrophilic chromatographic solvent is established through chromatographic column 38, reverse phase fractionation of the peptide digests is carried out by gradually increasing the amount of hydrophobic chromatographic solvent from container 64 in the flow. In preferred embodiments of the invention, reverse phase fractionation is accomplished by increasing the amount of hydrophobic chromatographic solvent using a 2% linear gradient from 100% hydrophilic chromatographic solvent to a combination of 60% hydrophilic chromatographic solvent and 40% hydrophobic chromatographic solvent over 20 minutes at a flow rate of 1 ml/minute. As the amount of the hydrophobic chromatographic solvent in the flow is increased, selective solubilization of the peptides loaded onto column 38 occurs. Generally, the smaller peptides tend to be more soluble at lower concentrations of the hydrophobic chromatographic solvent than the larger peptides such that interaction between the chromatographic medium of column 38 and the smaller peptides is broken first. As a result, the smaller peptides are eluted through column 38 prior to the larger peptides, thus resulting in fractionation of the peptides in the effluent being discharged from column 38.

The effluent from chromatographic column 38 is transported to mass spectrometer 48 and subjected to mass spectroscopic analysis in which a mass spectroscopic data set is generated. Such a data set is often referred to as an "HPLC-MS data set" when spectroscopic analysis of the peptide digests is carried out after HPLC fractionation of the peptide digests. The mass spectroscopic data set should contain sufficient data such that a plurality of selective ion chromatograms for a plurality of peptide digests can be computed and used to derive values indicative of the relative abundance of any one or more of the peptide digests. Generally, scanning in the m/z range from 200 to 2000 at a scan rate of 3 seconds would be suitable in the practice of the present invention. The mass spectroscopic data set can be generated in any convenient data format. As one example, we have found that generating the data set in the AIA andi standard format is suitable in the practice of the present invention.

Still referring to FIG. 6, the mass spectroscopic data set is analyzed using computer system 54. Computer system 54 includes programming comprising instructions enabling computer system 54 to compute the selective ion chromatograms from the mass spectroscopic data set, to derive values indicative of the relative abundance of the digests from such selective ion chromatograms, and to compare such values for one protein sample to corresponding values of another protein sample or to the corresponding values of a reference protein. In a preferred embodiment, the program comprises instructions enabling computer system 54 to analyze the mass spectroscopic data set according to the six-step process described below. In the following discussion, the data is assumed to be in the AIA andi format for purposes of the discussion.

Step 1: The program is provided with a data file in text format comprising a list of one or more peptide digests expected to be seen as a product of the enzymatic digestion of the protein sample. For each peptide digest included in the list, the list would including a corresponding mass interval for which each such peptide digest is expected to elute from column 18 and be detected by mass spectrometer 28. The list preferably includes (a) at least one peptide digest which is known to undergo modification, and (b) either (i) one or more peptide digests which are variants of such intended peptide digest, and/or (ii) a reference peptide digest. For example, referring to FIG. 2, the list preferably would include peptide digest 6a'. The list would further include one or more of the variants 6b' and 6c' and/or a reference peptide digest such as peptide digest 3'.

The mass interval to be included in the list is preferably defined as a particular atomic mass unit (amu) plus or minus a mass variability term typically selected to be in the range from ±0 to ±1, preferably about ±0.5 amu. The retention time interval to be included in the list is preferably defined in one of two ways. As one option, the retention time interval may be defined as substantially the entire time interval in which elution of the peptide digest is expected to occur. As an alternative option, the retention time interval may be defined as the interval in which the chromatographic peak maximum is expected to occur. In such alternative option, the program would desirably include instructions for identifying the beginning and end of the peak so that a corresponding peak area may be calculated. The boundaries of a peak area may be defined in any convenient manner as long as boundaries are defined in a consistent manner for all selective ion chromatograms. As one method for defining peak area boundaries, defining retention time interval boundaries as the time points corresponding to intensity values of the range from 1 to 20%, preferably 5 to 15%, and more preferably about 10% of the peak maximum have been found to be suitable in the practice of the present invention.

Step 2: Suitable program instructions are used to read data from the peptide digest data file. The program instructions also read the mass spectroscopic data set using standard library routines. Program instructions for reading the data list and data set are known in the art and suitable instructions could be selected in accordance with conventional practices.

Step 3: Program instructions compute selective ion chromatograms for one or more mass intervals corresponding to the m/z intervals of the peptide digests listed in the peptide digest data file. A variety of program instructions for computing selective ion chromatograms are known in the art and could be used to compute the selective ion chromatograms in the practice of the present invention. As one example, the C program referred to above has been found to be effective for this purpose.

Step 4: Each selective ion chromatogram is post—processed in order to accomplish baseline removal and noise filtering. Baseline removal is accomplished by computing a baseline chromatogram for each selective ion chromatogram, which is then subtracted from the selective ion chromatogram. The baseline chromatogram for each selective ion chromatogram preferably is computed by low pass filtering the selective ion chromatogram using a finite impulse response (FIR) filter or by using discrete wavelet transforms (DWT's). In embodiments using DWT's, a DWT transform is initially computed and only the large scale (low frequency) wavelet coefficients are retained prior to performing the inverse DWT. It has been reported that using DWT's to generate a baseline tends to produce better baseline chromatograms than the FIR filtering method. See, e.g., Barclay, V. J., Bonner, R. F., Thibault, P., Application of Wavelet Transforms to Electrospray Spectra: Baseline Removal, ASMS, May 1996 (Barclay I); and Barclay, V. J., Bonner, R. F., Hamilton, I. P., Application of Wavelet Transforms to Electrospray Spectra: Denoising, Smoothing, and Compression, ASMS, May 1996 (Barclay II). Prior to subtracting the baseline chromatogram from the selective ion chromatogram, the baseline chromatogram is appropriately scaled such that the subtraction of the baseline from the selective ion chromatogram will not result in any values less than zero.

High frequency noise filtering can be accomplished using digital filtering or discrete wavelet transforms (DWT's). In the case of using digital filtering, a low pass FIR filter can be used to attenuate high frequency noise on a baseline subtracted chromatogram. In the case of using discrete wavelet transforms, discrete wavelet transform coefficients that fall below a computed noise threshold can be shrunk to zero prior to performing an inverse DWT in order to attenuate high frequency noise terms. See, e.g., Donoho, D. L., Johnstone, I. M., Adapting to Unknown Smoothness via Wavelet Shrinkage, *Journal of the American Statistical Association*, 90, 1200–1224, 1995. In general, shrinkage of DWT coefficients has been reported to be superior to filtering methods in reducing high frequency noise. The use of both FIR filters and discrete wavelet transforms to compute chromatographic baselines and reduce high frequency noise in chromatograms has previously been reported. See, e.g., Barclay I and II.

Step 5: Program instructions integrate each of the selective ion chromatograms in the corresponding retention time interval listed on the peptide digest data file. Integration is accomplished using a suitable integration technique such as Simpson's rule or the trapezoid rule. The C program may be used to accomplish such integration. As an alternative to integrating over the retention time interval specified in the peptide digest data file for each defined peptide digest, it is preferred to locate peaks on the selective ion chromatograms using an automatic peak picking algorithm in order to identify the retention time interval over which the peptide digest is actually eluting. This alternative is preferred because actual retention times observed for the peptide digests may not be the same as the retention time intervals listed on the peptide digest data file. When peak picking using an algorithm, the retention time of the identified peak center is compared to the corresponding retention time interval specified in the peptide digest data file to ensure that the correct peak was selected (On rare occasions, multiple peaks may be found in a selective ion chromatogram as shown in FIG. 5.). When chromatographic peaks of a selective ion chromatogram are identified by locating a peak center falling within a particular retention time interval, either automatically or by reference to a retention time interval recited in the peptide digest data file, peak area can be computed by integrating the area under such peak extending between the time points on either side of the peak maximum corresponding to the intensity values in the range from 0 to 20%, preferably 5 to 15%, and more preferably about 10% of the peak maximum.

There are several known algorithms for automatically identifying peaks in a chromatogram, including derivative-based methods and polynomial fitting methods. Derivative-based methods and polynomial fitting methods have been reported in the literature and are the most commonly reported way to identify peaks. The present invention also provides an additional, novel approach for peak picking which identifies chromatographic peaks using discrete wavelet transform (DWT) methods. The use of discrete wavelet transforms to detect changes (e.g. sharp jumps) in a signal has been reported in the statistics literature, see Wang, Y., Jump and Sharp Cusp Detection By Wavelets, *Biometrika*, 82, 385397,1995, but the present inventors are not aware of any references which suggest using DWT's for identifying chromatographic peaks. According to this novel approach, DWT's are used to locate chromatographic peaks by identifying small scale (high frequency) DWT coefficients that are above a noise level threshold.

Step 6: Program instructions, write the result of each integration to an ASCII text file. The integration results are then read into a spreadsheet where values indicative of the relative abundance of one or more peptide digests, e.g., ratios of peak areas, are derived from the integration results. Such values are compared to the corresponding values associated with a reference protein or with one or more other protein samples which have been digested, fractionated, and subjected to mass spectroscopic analysis in a similar fashion, or to ranges recited in a product specification, or the like. Significant similarities and/or differences in the values may be outputted in any convenient format, e.g., either visually on a display screen or in printed form. Depending upon the significance of such similarities and differences, the outputted information may lead to further investigations to further characterize such differences.

In addition to the six-step process described above, the present invention also provides an alternative method for qualitatively comparing two complex mixtures, e.g., mixtures comprising a plurality of peptide digests obtained by enzymatic digestion of protein samples to be compared. Although this alternative method advantageously applies to comparisons of any complex mixtures using any separation technique (e.g. gas chromatography (GC), liquid chromatography (LC), capillary electrophoresis (CE) and the like) and/or any detection method (e.g. MS, UV-Vis, and the like), the method will be described with respect to comparisons of fractionated peptide digest mixtures subjected to mass spectroscopic analysis.

As an overview, with reference to system 30 of FIG. 6, this alternative method includes digesting protein samples to be compared, preferably fractionating the digests, subjecting the digests to mass spectroscopic analysis, identifying substantially all of the mass spectroscopic peaks for the samples, matching peaks between the two samples based on mass (or wavelength in the case of other spectroscopic analysis techniques) and chromatographic profile, and reporting the results of such peak matching. In some embodiments, the step of identifying substantially all of the mass spectroscopic peaks for each sample comprises computing a plurality of selective ion chromatograms for the samples to be compared and then identifying substantially all of the peaks in all such selective ion chromatograms. In such embodiments, peaks of such selective ion chromatograms would be matched.

The results of peak matching may be reported in a variety of formats. For example, if it is desired to report unmatched peaks, the unmatched peaks may be reported in a list format with their retention time, peak, width, and mass details. Alternatively, unmatched peaks may be reported in a reconstructed three dimensional data file where the unmatched peaks in one sample are placed in a first pseudo-LC-MS data file for plotting and the unmatched peaks in a second sample are placed in a second pseudo-LC-MS data file for plotting.

An advantage of this alternate method over the six-step method described above is that no prior knowledge of the samples to be compared is required (i.e. no pre-defined list of peptide digests needs to be created). As another advantage, this method is capable of identifying more differences between the samples than just those resulting from analysis of the peptide digests of the pre-defined list. Because this alternative method is general in that no prior sample knowledge is required, it is applicable to many other applications of HPLC-MS sample comparisons (e.g. natural products, quality control, environmental monitoring, etc.).

To implement this alternative comparison method using system 30 of FIG. 5, each protein sample is digested, the resultant peptides fractionated and subjected to mass spectroscopic analysis as described above. However, for practicing this alternative method of the claimed invention, computer system 54 of FIG. 6 includes programming comprising instructions enabling computer system 54 to compute the selective ion chromatograms for each sample, to automatically identify peaks of such selective ion chromatograms, to automatically match peaks between the selective ion chromatograms of the two samples, and to output information relating to the peak matching. In a preferred embodiment, the program comprises instructions enabling computer system 54 to analyze the mass spectroscopic data set according to the preferred seven-step process described below. In the following discussion, the data is assumed to be in the AIA andi file format for illustrative purposes.

Step A: The first step for comparing first and second mass spectroscopic data sets is to align the retention time of one sample relative to the other sample. This alignment is required to correct for the retention time variability between sample runs which tends to occur due to column aging, temperature effects, and the like. Because the samples used for comparison may not necessarily contain consistent data to use for alignment, it is preferred to align off of standard mixtures that are analyzed prior to the analysis of each sample. Use of such standards assumes that the column changes between analysis of a standard and subsequent analysis of the corresponding sample are negligible. This is a reasonable assumption when the analysis of a sample follows an analysis of a standard closely in time. The standard mixture contains well-characterized peaks that elute over the entire retention time range, and such peaks can be used for retention time alignment. To accomplish alignment, the standards and samples are subjected to mass spectroscopic analysis and then total ion chromatograms for a standard example are computed from the resultant data. Given the total ion chromatograms (TIC's) for each standard mixture associated with each sample, a dynamic time warping algorithm is used to align one standard mixture relative to the other standard mixture. Dynamic time warping algorithms have been described, for example, in Wang, C. P., Isenhour, T. L., Time-Warping Algorithm Applied to Chromatographic Peak Matching Gas Chromatography/Fourier Transform Infrared/Mass Spectrometry, *Analytical Chemistry*, 59, 649–654, 1987; and Sakoe, H., Chiba, S., *IEEE Trans. Acoust., Speech, Signal Process., ASSP*-26, 43 49, 1978. The same alignment function is then used to align the samples to be compared. The dynamic time warping algorithm begins alignment by windowing corresponding sections of the TIC of each standard mixture using a windowing function, such as a Hamming window, to de-emphasize any peaks near the window boundary. This windowing is performed so that peaks present at the window boundary do not influence the alignment process. The windowed sections of the TIC from each standard mixture are then cross-correlated and the time shift associated with the maximum cross-correlation value is chosen as the optimal retention time shift to apply at the current window position. The window is then moved along the retention time axis and the process is repeated until alignment across the full range of the TIC is accomplished.

Step B: Following retention time alignment, peak grouping of the mass spectroscopic data set of each sample data is performed to ensure that high quality selective ion chromatograms are generated. Simply computing peaks using only those fragments that fall within a specified mass interval for a selective ion chromatogram produces poor quality chromatograms when the mass of fragments in adjacent scans are oscillating around the boundary of the mass interval for the selective ion chromatogram. The resultant effect of this problem is a dropout in the selective ion chromatogram when this oscillation is occurring. To avoid this dropout problem, the present invention uses a novel fragment grouping algorithm described below.

The fragment grouping algorithm is based upon the concept of assigning each detected fragment to a fragment group having a designated mass interval corresponding to the mass associated with such detected fragment. Selective ion chromatograms are advantageously computed from information comprising such fragment groups. A fragment group for a particular mass interval is first opened when a fragment having a mass outside of the mass interval of any currently open fragment group is detected. A fragment group remains open, and fragments are assigned to such fragment group, until a designated number of scans (the scan closure number) are processed without any fragments being assigned to the group.

The size of the mass interval for the various fragment groups and the scan closure number applicable to closing the fragment groups can each be designated by the operator and can be varied to optimize the quality of the selective ion chromatograms to be computed from information comprising such fragment groups. Selecting appropriate mass interval sizes and scan closure numbers depends upon a variety of factors including the nature of the sample under investigation, the scan rate, the sensitivity of the instrument used to collect the data, and the like. Generally, with respect to selecting appropriate mass intervals for purposes of assigning fragments to the fragment groups, one suitable approach is to assign a mass interval of M+/−Dm to each fragment group, wherein M is the mass associated with the first fragment assigned to the fragment group and Dm is a mass variability term having a value in the range from 0.25 to 5, preferably 0.5 to 3, and more preferably 0.5 to 1.0 mass units. The scan closure number is preferably in the range from 1 to 5, more preferably 2 to 3, consecutive scans.

The preferred mode of operation of the fragment grouping algorithm will now be described with respect to FIGS. 7a–7d. FIGS. 7a–7d are a schematic representation of mass spectroscopic data, generally designated as 100, collected for the fractionated peptide digests of a protein sample. For purposes of clarity and illustration, data from only four consecutive scans 101, 102, 103, and 104 are shown in the Figures. In actual practice, hundreds of scans are typically made. At the outset, no fragment groups are open. Also, if not already entered, the operator at the outset may select a scan closure number and a mass variability term. For purposes of this discussion concerning FIGS. 7a–7d, it is assumed that a scan closure number of 1 and mass variability term of +/−0.5 mass units were selected by the operator, although other suitable values could be selected as desired. The algorithm begins by examining the first scan 101. In this case, fragment 108 having an associated mass of $M_1$ was detected. Inasmuch as no fragment groups are yet open, a new fragment group having a designated mass interval of $M_1$+/−0.5 is opened and the fragment 108 is assigned to that fragment group. For the next scan 102, fragment 110 having the mass $M_1$+0.3 and fragment 112 having mass $M_2$ were detected. Fragment 110 is assigned to the fragment group having the mass interval of $M_1$+/−0.5, and fragment 112 is assigned to a new fragment group having a designated mass interval of $M_2$+/−0.5. In the third scan, no fragment having a mass of $M_1$ was detected and so the fragment group having a mass interval of $M_1$+/−0.5 is closed. Fragment 114 having a mass of $M_2$+0.4 was detected, however, and is assigned to the fragment group having a mass interval of $M_2$+/−0.5. In the fourth scan 104, no fragments were detected and so the open fragment group having a mass interval of $M_2$+/−0.5 is closed. The fourth scan 104 was the last scan acquired and so the algorithm is now finished assigning fragments to fragment groups.

After a portion, and preferably all, of the scans have been processed, selective ion chromatograms may be computed from information comprising the fragment groupings. In order to identify each resultant selective ion chromatogram with the mass interval for which such chromatogram was computed, each selective ion chromatogram can be assigned a mass label corresponding to such mass interval. Given that most fragment groups in actual practice tend to include a plurality of fragments, a mass label should be selected which is representative of all fragments included in the group. For example, in the case of the fragment group having the mass interval $M_2$+/31−0.5, the single ion chromatogram can be assigned a mass label of $M_2$ if desired. As an alternative, the selective ion chromatogram can be assigned a mass label which is an average of all masses associated with all fragments assigned to the corresponding fragment group. For example, for the selective ion chromatogram derived from the fragment group having a mass interval of $M_2$+/−0.5, fragments having masses of $M_2$ and $M_2$+0.4 were assigned to the fragment group. If the selective ion chromatogram is to be assigned an average mass label derived from such masses, such average mass in this case would be $M_2$+0.2. The masses of individual fragments are then redesignated to have a mass equal to the corresponding fragment group mass label. Such redesignation is done prior to selective ion chromatogram generation to ensure that no dropouts occur.

Step C: Following fragment grouping to eliminate dropouts, the selective ion chromatograms are computed for each sample using a pre-specified mass step size (e.g. 1 amu) between successive selective ion chromatograms. The advantages of computing selective ion chromatograms using the novel fragment grouping algorithm will now be further described with respect to the exemplary data shown in Table 1. Table I displays a series of masses detected from adjacent HPLC-MS scans.

TABLE 1

Example of Oscillating Mass From Adjacent UPLC-MS Scans

| Scan | Mass |
| --- | --- |
| 100 | 434.48 |
| 101 | 434.49 |
| 102 | 434.48 |
| 103 | 434.52 |
| 104 | 434.44 |
| 105 | 434.46 |

FIG. 8 shows the resulting selective ion chromatogram computed for a mass interval of 433.5 to 434.5 (i.e., the mass interval around 434) and the dropout caused by the fragment in scan 103 which is outside the upper selective ion chromatogram mass boundary of 434.5. FIG. 9 shows the same selective ion chromatogram computed using the fragment grouping algorithm of the present invention to eliminate such selective ion chromatogram dropout. The dropout is eliminated in FIG. 9 because the boundaries of the pertinent fragment group are defined in terms of the first fragment that was put into such group, in this case 434.48, rather than an arbitrary number such as "434".

Step D: Each selective ion chromatogram for each sample is then processed to remove baseline drift and high frequency noise using either digital FIR filtering or discrete wavelet transforms (DWT's) as discussed above.

Step E: A peak picking algorithm is then applied to every selective ion chromatogram for each sample to identify chromatographic peaks. The peak picking can be accomplished with any of the methods specified above (derivative methods, polynomial fitting methods, or DWT methods).

Step F: Each peak identified in the selective ion chromatograms of the first sample is then matched against all peaks in the second sample. Corresponding peak pairs are identified as a result. Additionally, unmatched peaks are also identified. The matching is done via a matching function that defines the similarity between two peaks. The matching is accomplished based upon a variety of factors associated with the peaks and the chromatographic profile of the peaks. The difference between the average mass corresponding to each peak is also factored into the matching function since there will be multiple masses eluting at the same time when a protein sample has undergone fragmentation by enzymatic digestion.

Step G: After pairs of peaks have been matched between the two samples, the results are outputted in any desired fashion. For example, unmatched peaks may be listed and written out to a report which is printed and/or visually displayed on a display screen. The information in such a report may include, for example, peak area, peak start time, peak end time, average mass of peak, and the sample from which the peak was found. Results may also be outputted in graphic form. For example, a pseudo-HPLC-MS data set may be created using only the data contained in the unmatched peaks. Two such data sets can be created: one containing data from peaks found in the first sample but not the second sample and another containing data from peaks found in the second sample but not the first sample. These pseudo-HPLC-MS data sets may then be plotted using any HPLC-MS data plotting tool (e.g. total ion chromatogram, slicing of total ion chromatogram, contour plot, surface, etc.)

As an alternative to the above steps A through G, peak matching can also occur by an approach in which the HPLC-MS data set is viewed as a 3-D contour plot. Using standard 3-D peak picking algorithms (such as those used in NMR spectroscopy and similar peak matching approaches), unmatched peaks between two different 3-D contour plots can be identified.

The present invention will now be further described with regard to the following example:

EXAMPLE

Recombinant hemoglobin therapeutically functions as an oxygen carrier in circumstances of trauma or other instances needing normal human hemoglobin supplements. The recombinant hemoglobin molecule is very similar to human hemoglobin in that recombinant hemoglobin has two beta globin proteins, two alpha globin proteins, and 4 heme cofactors. However, in recombinant hemoglobin, the two alpha globin proteins are fused with additional amino acids. Other slight modifications in the amino acid sequence of the globin chains are also present in the recombinant hemoglobin molecule. The recombinant hemoglobin is very complex due to the very large size of the protein. It has a molecular mass in excess of 60,000 daltons compared to other recombinant proteins, such as biosynthetic human insulin or glucagon, which have molecular masses of 5800 and 3500 daltons, respectively. Due to the large size of the recombinant hemoglobin molecule, and due to the large number of modifications to the molecule which may occur post-translationally or during (i) isolation, (ii) purification, or (iii) product storage, it is very difficult to analytically characterize recombinant hemoglobin to the same extent as less complex molecules, such as biosynthetic human insulin, when using previously known analytical methods.

Four different recombinant hemoglobin (rHb1.1) samples (Samples 1–4, respectively) were produced, each as a soluble protein in *E.coli*. Of the four samples, Sample 1 represents the intended form of the protein product, and thus serves as a reference to which the other three samples may be compared. Each sample contained unintended modifications to the primary sequence of the globin chains. For example, the peptides at the Beta-T1 position were known to have undergone five modifications: norleucine substitution for methionone (Nle-1); unintended oxidation of the N-terminus methionone (Met(O)-1); acetylation of the N-terminus methionone (N-acetylation); unintended pyruvylation of the N-terminus methionone which increased the molecular mass of the peptide by 70 daltons (M+70); and norvaline misincorporation for leucine at the third position (Nvl-3). Thus, the peptide at the Beta-T1 position was likely to be present in its intended form as well as in the forms of the five variants. Similarly, the peptides at the Dialpha-T1&T2 position were known to have undergone Nle-1, Met(O)-1, and M+70 modifications. Thus, the peptide at the Dialpha-T1&T2 position was likely to be present in its intended form as well as in the forms of the three variants.

To quantitatively characterize these modifications, the four samples were analyzed using a system configured in accordance with system 30 of FIG. 6. Thus, each sample was enzymatically digested using an on-line enzymatic digestion column commercially available as the Porozyme™ Immobilized Trypsin Cartridge from Perspective Biosystems. The resultant tryptic peptide digests were fractionated using reverse phase HPLC techniques on a Vydac™ C-18 HPLC column available from the Separations Group. The fractionated peptide digests were then subjected to mass spectroscopic analysis using a Finnegan SSQ 710C single stage quadrupole mass spectrometer with an electrospray source.

To characterize the modifications at Beta-T1, a predefined list comprising the six forms of the Beta-T1 peptide, corresponding masses, and corresponding retention time intervals was provided. To characterize the modifications at Dialpha-T1&T2, the predefined list also included comparable information for the four forms of the Dialpha-T1&T2 peptide. Using the information from the list, a selective ion chromatogram for each listed peptide was computed and then integrated in the corresponding retention time interval to obtain a peak area for the corresponding peptide digest. The relative abundance of the peptides at Beta-T1 were then computed according to the following expression:

$$\frac{A_i}{A_1 + A_2 + A_3 + A_4 + A_5 + A_6}$$

wherein $A_i$ is the peak area of the particular peptide digest of interest, $A_1$ is the peak area of the intended form of the peptide digest, $A_2$ is the peak area of the Nle-1 variant, $A_3$ is the peak area of the Met(O)-1 variant, $A_4$ is the peak area of the N-acetylation variant, $A_5$ is the M+70 variant, and $A_6$ is the Nvl-3 variant. The results are shown in the following table:

TABLE II

Percent Relative Abundance of Peptide Forms at Beta-T1

| Peptide Form | % of relative abundance | | | |
|---|---|---|---|---|
| | Sample 1 | Sample 2 | Sample 3 | Sample 4 |
| Intended form | 94.4 | 95.0 | 90.3 | 70.7 |
| Nle-1 variant | 0.0 | 0.0 | 2.1 | 4.5 |
| Met(O)-1 variant | 1.0 | 1.5 | 1.1 | 1.7 |
| N-acetylation | 3.9 | 3.1 | 5.0 | 9.4 |
| M + 70 | 0.7 | 0.4 | 0.9 | 13.7 |
| Nvl-3 | 0.0 | 0.0 | 0.6 | 0.0 |

In a similar fashion, the relative abundances of the peptides at Dialpha-T1&T2 were computed according to the following expression:

$$\frac{A_j}{A_7 + A_8 + A_9 + A_{10}}$$

wherein $A_j$ is the peak area of the particular peptide digest of interest, $A_7$ is the peak area of the intended form of the peptide digest, $A_8$ is the peak area of the Nle-1 variant, $A_9$ is the peak area of the Met (O)-1 variant, and $A_{10}$ is the peak area of the M–70 variant. The results are shown in the following table:

TABLE III

Percent Relative Abundance of Peptide Forms at DiAlpha - T1 & T2

| Peptide Form | % of relative abundance | | | |
|---|---|---|---|---|
| | Sample 1 | Sample 2 | Sample 3 | Sample 4 |
| Intended form | 97.4 | 97.3 | 96.7 | 83.6 |
| Nle-1 variant | 0.3 | 0.0 | 0.8 | 2.9 |
| Met(O)-1 variant | 1.1 | 1.7 | 1.5 | 4.5 |
| M + 70 variant | 1.0 | 1.0 | 1.0 | 9.0 |

The data shows that the present invention can be used to provide meaningful quantitative information concerning the composition of protein samples. This, in turn, allows meaningful quantitative comparisons between different protein samples to be easily made. For example, with respect to the Beta-T1 and DiAlpha-T1&T2 data, it can be seen that Samples 2 and 3 are very comparable to Sample 1. Sample 2 includes a slightly higher content of the Met(O) variants relative to sample 1. The data for Sample 3 shows that Sample includes norleucine misincorporated for the N-terminal methiononoes as well as norvaline misincorporation for leucine at the third position at higher levels than are present in Sample 1. Sample 4 is very dissimilar to Sample 1 in almost every respect, clearly indicating that Sample 4 is a material not appropriate for use.

Notice how the ability of the present invention to provide this kind of quantitative data would allow product specifications to be prepared which could specify acceptable relative abundances of the various peptide variants. Thus, the present invention provides an excellent tool for monitoring the quality of production proteins.

The data provided above relates to the N-terminal peptides. However, the present invention makes it possible to quantitatively analyze any peptide for modifications resulting from a change in molecular mass throughout the entire sequence of recombinant hemoglobin or any other protein molecule, as desired. The present invention is particularly advantageously used to characterize any protein which cannot be characterized by simple resolution of components by chromatographic methods. Additionally, the present invention makes it easy to identify and monitor protein modification trends which may result from a process change. Thus, one could gauge the effect of a process change upon a modification. For example, one could gauge whether the use of reducing agents during production actually reduces oxidative damage. Without the techniques provided by the present invention, this kind of data would be much more difficult, and even impossible, to obtain by the previously known methods.

While this invention has been described with respect to preferred embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An apparatus for analyzing a protein sample, comprising:
   (a) a reactor vessel comprising an enzyme activity capable of digesting the protein sample in order to provide a plurality of peptide digests, an inlet port for receiving the protein to be digested, and an exit port for discharging the peptide digests;
   (b) a chromatographic column comprising a chromatographic medium capable of chromatographically fractionating the peptide digests as the peptide digests are eluted through the column, wherein the chromatographic column comprises an inlet port for receiving the peptide digests, said inlet port being in flow communication with the exit port of the reactor vessel, and wherein the chromatographic column comprises an exit port for discharging an effluent comprising the chromatographically fractionated peptide digests;
   (c) a mass spectrometer capable of generating a mass spectroscopic data set, wherein said mass spectrometer has an inlet port for receiving the chromatographically fractionated peptide digests, said inlet port being in flow communication with the exit port of the chromatographic column;
   (d) a computer system operationally coupled to the mass spectrometer such that the computer system is capable of analyzing said mass spectroscopic data set, wherein the computer system comprises a program comprising:
      (i) instructions enabling said computer system to compute a plurality of selective ion chromatograms, wherein said selective ion chromatograms are derived from said mass spectroscopic data set;
      (ii) instructions enabling said computer system to compute a plurality of peak areas of said selective ion chromatograms; and
      (iii) instructions enabling said computer to calculate at least one value indicative of the abundance of at least one of the peptide digests, wherein said value is derived from information comprising at least two peak areas selected from a peak area of an intended form of a peptide digest, a peak area of a first variant of said intended form of a peptide digest, a peak area of a second variant of said intended form of a peptide digest, and a peak area of a reference peptide digest.

2. The apparatus of claim 1, wherein said program further includes:

(a) a data file comprising a predefined list of a plurality of peptide digests expected to be seen as a result of enzymatic digestion of the protein sample by the enzyme activity, wherein said predefined list comprises at least two peptide digests selected from an intended form of a peptide digest, a first variant of said intended form of a peptide digest, a second variant of said intended form of a peptide digest, and a reference peptide digest, and wherein, for each peptide digest of the listed plurality of peptide digests, the list further includes a corresponding mass interval and a corresponding retention time interval for which each such peptide digest is expected to be detected by the mass spectrometer;

(b) instructions enabling the computer system to determine a retention time interval over which at least one peak area is calculated by reading the retention time interval from the data file; and (c) instructions enabling the computer system to determine a mass interval for which at least one selective ion chromatogram is to be computed by reading the mass interval from the data file.

3. The apparatus of claim 1, wherein the program further comprises instructions enabling the computer system to determine a retention time interval over which at least one peak area is to be calculated by reading the retention time interval from a data file comprising a predefined list of a plurality of peptide digests expected to be seen as a result of enzymatic digestion of the protein sample by the enzyme activity and a list of corresponding retention time intervals for which each such peptide digest is expected to be detected by the mass spectrometer.

4. The apparatus of claim 1, wherein the program further comprises instructions enabling the computer system to determine a mass interval for which at least one selective ion chromatogram is to be computed by reading the mass interval from a data file comprising a predefined list of a plurality of peptide digests expected to be seen as a result of enzymatic digestion of the protein sample by the enzyme activity and a list of corresponding mass intervals for which each such peptide digest is expected to be detected by the mass spectrometer.

5. The apparatus of claim 1, wherein the program further comprises a peak picking subprogram comprising instructions enabling the computer system to automatically locate the chromatographic peaks and corresponding retention time intervals of a plurality of the selective ion chromatograms such that the computer system can calculate peak areas of said chromatographic peaks over the corresponding retention time intervals.

6. The apparatus of claim 5, wherein the peak picking subprogram further comprises instructions enabling the computer system to automatically locate chromatographic peaks of a plurality of the selective ion chromatograms using information comprising discrete wavelet transforms.

7. The apparatus of claim 1, wherein said value indicative of the relative abundance of at least one of the peptide digests is derived from information comprising a ratio derived from a plurality of said peak areas.

8. The apparatus of claim 1, wherein the program further includes instructions enabling the computer system to compare said at least one relative value to corresponding one or more relative values obtained for at least one other protein sample.

9. The apparatus of claim 1, wherein the enzyme activity comprises trypsin.

10. The apparatus of claim 7, wherein the trypsin is immobilized in the reactor vessel.

11. The apparatus of claim 1, wherein the reactor vessel is an on-line enzyme digestion column.

12. The apparatus of claim 1, wherein the reactor vessel is a porozyme trypsin column.

13. The apparatus of claim 1, wherein the chromatographic column comprises a hydrophobic chromatographic medium onto which the peptide digests can be loaded in order to carry out reverse phase chromatographic fractionation of the peptide digests using a reverse phase solvent system comprising a relatively hydrophobic solvent and a relatively hydrophilic solvent.

14. An apparatus for comparing a first protein sample to a second protein sample, comprising:

(a) a reactor vessel comprising an enzyme activity capable of digesting each protein sample in order to provide a plurality of peptide digests corresponding to each of the samples, an inlet port for receiving the protein sample to be digested, and an exit port for discharging the corresponding peptide digests;

(b) a chromatographic column comprising a chromatographic medium capable of chromatographically fractionating the peptide digests resulting from the digestion of each protein sample, wherein the chromatographic column comprises an inlet port for receiving the peptide digests, said inlet port being in flow communication with the exit port of the reactor vessel, and wherein the chromatographic column comprises an exit port for discharging an effluent comprising the chromatographically fractionated peptide digests;

(c) a mass spectrometer capable of generating a mass spectroscopic data set, wherein said mass spectrometer has an inlet port for receiving the chromatographically fractionated peptide digests, said inlet port being in flow communication with the exit port of the chromatographic column;

(d) a computer system operationally coupled to the mass spectrometer such that the computer system is capable of analyzing said mass spectroscopic data set generated for each plurality of peptide digests, wherein the computer system comprises a program comprising:

(i) instructions enabling the computer system to compute a first plurality of selective ion chromatograms corresponding to the plurality of digests of the first protein sample and a second plurality of selective ion chromatograms corresponding to the plurality of digests of the second protein sample, wherein the first plurality of selective ion chromatograms is derived from the mass spectroscopic data set generated for the peptide digests of the first protein sample, and the second plurality of selective ion chromatograms is derived from the mass spectroscopic data set generated for the peptide digests of the second protein sample;

(ii) peak picking instructions enabling the computer system to automatically locate chromatographic peaks of the first and second pluralities of selective ion chromatograms;

(iii) instructions enabling the computer system to automatically match peaks between the first and second pluralities of selective ion chromatograms in order to identify matching peak pairs of the first and second pluralities of selective ion chromatograms; and (iv) instructions enabling the computer system to output results of said peak matching.

15. The apparatus of claim 14, wherein the program further includes instructions for automatically identifying a retention time interval for each of the chromatographic peaks and for calculating the peak area for each of the chromatographic peaks over the corresponding retention time interval.

16. The apparatus of claim 14, wherein the program further includes instructions enabling the computer system to align the retention time of the mass spectroscopic data set generated for the first plurality of peptide digests relative to the retention time of the mass spectroscopic data set generated for the second plurality of peptide digests.

17. The apparatus of claim 16, wherein the instructions for aligning the retention times of the first and second protein samples further comprises instructions enabling the computer system to align the retention time for the samples using a standard mixture as a reference for each sample.

18. The apparatus of claim 16, wherein the instructions for aligning the retention times of the first and second protein samples further comprise instructions enabling the computer system to accomplish retention time alignment using a dynamic time warping algorithm.

19. The apparatus of claim 14, wherein the program further includes instructions enabling the computer to accomplish fragment grouping of peptide digests detected by the mass spectrometer, wherein said fragment grouping instructions enable the computer system to assign the peptide digests to a plurality of fragment groups, wherein the peptide digests are assigned to fragment groups based upon the mass of the peptide digests, and wherein all peptide digests of each such fragment group are designated as having substantially the same mass value as all other peptide digests assigned to the same peak group.

20. The apparatus of claim 19, wherein the mass value of all peptide digests of a fragment group is designated to be substantially equal to the mass average of all peptide digests of the fragment group.

21. The apparatus of claim 19, wherein the instructions for computing the selective ion chromatograms comprise instructions enabling the computer system to compute the selective ion chromatograms using the designated mass values obtained from said fragment grouping.

22. The apparatus of claim 14, wherein the peak picking instructions comprise instructions enabling the computer system to automatically locate the chromatographic peaks of the selective ion chromatograms using information comprising discrete wavelet transforms.

23. A method of comparing a protein sample to a reference protein, comprising the steps of:
   (a) providing a predefined list of a plurality of peptides resulting from digestion of the reference protein by an enzyme activity, wherein said predefined list comprises at least two peptide digests selected from an intended form of a peptide digest, a first variant of said intended form of a peptide digest, a second variant of said intended form of a peptide digest, and a reference peptide digest, and wherein each of said peptides is characterized by a mass interval and a retention time interval for which each peptide is expected to be detected by a mass spectrometer;
   (b) characterizing the reference protein sufficiently such that the relative abundance of one or more of said plurality of peptides relative to one or more other peptides of the reference protein can be determined;
   (c) digesting the protein sample into a plurality of peptides using the enzyme activity;
   (d) fractionating the plurality of peptides resulting from digestion of the protein sample;
   (e) subjecting the fractionated peptides to mass spectroscopic analysis using a mass spectrometer in order to provide a mass spectroscopic data set from which a plurality of selective ion chromatograms for the fractionated peptide digests can be computed;
   (f) computing a plurality of selective ion chromatograms wherein the selective ion chromatograms are derived from the mass spectroscopic data set and wherein each of the selective ion chromatograms is computed for a mass interval corresponding to a mass interval of one of the plurality of listed peptides resulting from digestion of the reference protein;
   (g) calculating a plurality of peak areas of the selective ion chromatograms, wherein each peak area is calculated over a retention time interval corresponding to a retention time interval of one of the plurality of listed peptides resulting from digestion of the reference protein;
   (h) calculating a value indicative of the relative abundance of at least one fractionated peptide to the extent such fractionated peptide is detected by the mass spectrometer, wherein said relative abundance value is derived from information comprising a plurality of said peak areas of the selective ion chromatograms; and
   (i) comparing said value of said at least one peptide to the corresponding relative abundance value of the corresponding at least one peptide of the reference protein.

24. The method of claim 23, wherein the enzyme activity comprises trypsin.

25. The method of claim 23, wherein each of the steps of enzymatically digesting the protein sample occurs in a reactor vessel comprising an enzyme activity.

26. The method of claim 25, wherein the reactor vessel comprises an immobilized enzyme.

27. The method of claim 26, wherein the enzyme is trypsin.

28. The process of claim 27, wherein the reactor vessel is an on-line enzyme digestion column.

29. The method of claim 28, wherein the step of fractionating the plurality of peptides comprises the step of chromatographically fractionating the plurality of the peptides.

30. The method of claim 29, wherein the step of fractionating the plurality of peptides comprises the step of chromatographically fractionating each plurality of the peptides using reverse phase HPLC fractionation.

31. The method of claim 23, wherein said list is a data file stored in program instructions of a computer system, wherein said data file comprises the list of the plurality of peptide digests resulting from enzymatic digestion of the reference protein by the enzyme activity, and wherein, for each peptide digest of the listed plurality of peptide digests, the data file further includes the corresponding mass interval and the corresponding retention time interval for each of the peptides and wherein the method further comprises the steps of:
   (a) determining the retention time interval over which at least one peak area is calculated by reading the retention time interval from the data file; and
   (b) determining a mass interval for which at least one selective ion chromatogram is to be computed by reading the mass interval from the data file.

32. The method of claim 23, further comprising the step of determining a retention time interval over which at least one peak area is to be calculated by reading the retention time interval from a computer data file comprising a predefined list of a plurality of peptide digests expected to be seen as a result of enzymatic digestion of the protein sample by the enzyme activity and a corresponding retention time interval for which each such peptide digest is expected to be detected by the mass spectrometer.

33. The method of claim 23, further comprising the step of determining a mass interval for which at least one selective ion chromatogram is to be computed by reading the mass interval from a data file comprising a predefined list of a plurality of peptide digests expected to be seen as a result of enzymatic digestion of the protein sample by the enzyme activity and a corresponding mass interval for which each such peptide digest is expected to be detected by the mass spectrometer.

34. The method of claim 23, further comprising the step of using a peak picking algorithm to automatically locate the chromatographic peaks and corresponding retention time intervals of a plurality of the selective ion chromatograms such that a computer system can calculate peak areas of said chromatographic peaks over the corresponding retention time intervals.

35. The method of claim 34, wherein the peak picking algorithm comprises instructions enabling the computer system to automatically locate chromatographic peaks of a plurality of the selective ion chromatograms using information comprising discrete wavelet transforms.

36. The method of claim 23, wherein said value indicative of the relative abundance of at least one of the peptide digests is derived from information comprising a ratio of said peak areas.

37. A method of comparing a first protein sample to a second protein sample, comprising the steps of:
(a) digesting the first protein sample into a first plurality of peptides using an enzyme activity;
(b) digesting the second protein sample into a second plurality of peptides using the enzyme activity;
(c) fractionating each of the first and second pluralities of peptides;
(d) subjecting each of the first and second fractionated pluralities of peptides to mass spectroscopic analysis in order to generate a mass spectroscopic data set for each plurality of fractionated peptides from which a plurality of selective ion chromatograms for each plurality of fractionated peptides can be computed;
(e) computing a first plurality of selective ion chromatograms for the first plurality of fractionated peptides, wherein the first plurality of selective ion chromatograms is derived from the mass spectroscopic data set generated for the first plurality of fractionated peptides;
(f) computing a second plurality of selective ion chromatograms for the second plurality of fractionated peptides, wherein the second plurality of selective ion chromatograms is derived from the mass spectroscopic data set generated for the second plurality of fractionated peptides;
(g) automatically locating chromatographic peaks of the first and second pluralities of selective ion chromatograms;
(h) automatically matching peaks between the first and second pluralities of selective ion chromatograms in order to identify matching peak pairs; and
(i) outputting information indicating results of said peak matching.

38. The method of claim 37, wherein each of the steps of enzymatically digesting the first and second proteins occurs in a reactor vessel comprising an enzyme activity.

39. The method of claim 37, wherein the reactor vessel comprises an immobilized enzyme.

40. The method of claim 37, wherein the enzyme is trypsin.

41. The method of claim 37, wherein the reactor vessel is an on-line enzyme digestion column.

42. The method of claim 37, wherein the step of fractionating each plurality of the peptides comprises the step of chromatographically fractionating each plurality of the peptides.

43. The method of claim 37, wherein the step of fractionating each plurality of the peptides comprises the step of chromatographically fractionating each plurality of the peptides using reverse phase chromatographic fractionation on an on-line chromatographic column.

44. The method of claim 37, further comprises the steps of automatically identifying a retention time interval for each of a plurality of chromatographic peaks of the selective ion chromatograms and calculating a peak area for each of the chromatographic peaks over the corresponding retention time interval.

45. The method of claim 37; further comprising the step of aligning the retention time of the mass spectroscopic data set generated for the first plurality of peptide digests corresponding to the first protein sample relative to the retention time of the mass spectroscopic data set generated for the second plurality of peptide digests corresponding to the second protein sample.

46. The method of claim 45, wherein the step of aligning the retention times of the first and second protein samples comprises aligning the retention time for the samples using a standard mixture as a reference for each sample.

47. The method of claim 45, wherein the step of aligning the retention times of the first and second protein samples comprises accomplishing retention time alignment using a dynamic time warping algorithm.

48. The method of claim 37, comprising the step of peak grouping the peptide digests detected by the mass spectrometer, wherein said peak grouping comprises assigning the peptide digests to a plurality of peak groups, wherein the peptide digests are assigned to peak groups based upon the mass of the peptide digests, and wherein each peptide digest of each such peak group is designated as having substantially the same mass value as other peptide digests assigned to the same peak group.

49. The method of claim 48, wherein the designated mass value of all peptide digests of a peak group is substantially equal to the mass average of all peptide digests of the peak group.

50. The method of claim 48, wherein the selective ion chromatograms are computed using the designated mass values obtained from said peak grouping.

51. The method of claim 37, wherein the step of locating chromatographic peaks comprises locating the chromatographic peak using information comprising discrete wavelet transforms.

52. A method for analyzing an admixture of organic species, comprising:
(a) a chromatographic column comprising a chromatographic medium capable of chromatographically fractionating the organic species as the organic species are eluted through the column, wherein the chromatographic column comprises an inlet port for receiving the organic species, and wherein the chromatographic column comprises an exit port for discharging an effluent comprising the chromatographically fractionated organic species;
(b) a mass spectrometer capable of generating a mass spectroscopic data set comprising data from which a first plurality of selective ion chromatograms for the fractionated organic species can be generated, wherein said mass spectrometer has an inlet port for receiving the chromatographically fractionated organic species, said inlet port being in flow communication with the exit port of the chromatographic column;

(c) a computer system operationally coupled to the mass spectrometer such that the computer system is capable of analyzing said mass spectroscopic data set, wherein the computer system comprises a program comprising:

(i) instructions enabling said computer system to compute a plurality of selective ion chromatograms, wherein said selective ion chromatograms are derived from said mass spectroscopic data set;

(ii) instructions enabling said computer system to compute a plurality of peak areas of said selective ion chromatograms; and (iii) instructions enabling said computer to calculate at least one value indicative of the relative abundance of at least one of the organic species, wherein said value is derived from information comprising at least two peak areas selected from a peak area of an intended form of a peptide digest, a peak area of a first variant of said intended form of a peptide digest, a peak area of a second variant of said intended form of a peptide digest, and a peak area of a reference peptide digest.

53. An apparatus for comparing a first admixture of organic species to a second admixture of organic species, comprising:

(a) a chromatographic column comprising a chromatographic medium capable of chromatographically fractionating the organic species of each admixture, wherein the chromatographic column comprises an inlet port for receiving the admixtures, and wherein the chromatographic column comprises an exit port for discharging an effluent comprising the chromatographically fractionated organic species of each admixture;

(b) a mass spectrometer capable of generating a mass spectroscopic data set comprising data from which plurality of selective ion chromatograms for each fractionated admixture of organic species can be generated, wherein said mass spectrometer has an inlet port for receiving the chromatographically fractionated admixtures, said inlet port being in flow communication with the exit port of the chromatographic column;

(c) a computer system operationally coupled to the mass spectrometer such that the computer system is capable of analyzing said mass spectroscopic data set generated for each fractionated admixture, wherein the computer system comprises a program comprising:

(i) instructions enabling the computer system to compute a first plurality of selective ion chromatograms corresponding to the first organic admixture and a second plurality of selective ion chromatograms corresponding to the second admixture, wherein the first plurality of selective ion chromatograms is derived from the mass spectroscopic data set generated for the first admixture, and the second plurality of selective ion chromatograms is derived from the mass spectroscopic data set generated for the second admixture;

(ii) peak picking instructions enabling the computer system to automatically locate chromatographic peaks of the first and second pluralities of selective ion chromatograms;

(iii) instructions enabling the computer system to automatically match peaks between the first and second pluralities of selective ion chromatograms in order to identify matching peak pairs of the first and second pluralities of selective ion chromatograms; and (iv) instructions enabling the computer system to output results of said peak matching.

54. A method of comparing a sample admixture comprising a plurality of organic species to a reference admixture, comprising the steps of:

(a) providing a list of a plurality of organic species present in the reference admixture, wherein each of said organic species is characterized by a mass interval and a retention time interval for which each organic species is expected to be detected by a mass spectrometer;

(b) characterizing the reference admixture sufficiently such that the relative abundance of one or more of said organic species relative to one or more other organic species of the reference admixture can be determined;

(c) fractionating the organic species of the admixture sample;

(d) subjecting the fractionated organic species to mass spectroscopic analysis using a mass spectrometer in order to provide a mass spectroscopic data set from which a plurality of selective ion chromatograms for the fractionated organic species can be computed;

(e) computing a plurality of selective ion chromatograms, wherein the selective ion chromatograms are derived from the mass spectroscopic data set and wherein each of the selective ion chromatograms is computed for a mass interval corresponding to a mass interval of one of the plurality of listed organic species of the reference admixture;

(f) calculating a plurality of peak areas of the selective ion chromatograms, wherein each peak area is calculated over a retention time interval corresponding to a retention time interval of one of the organic species of the reference admixture;

(g) calculating a value indicative of the relative abundance of at least one fractionated organic species of the admixture sample to the extent such fractionated organic species is detected by the mass spectrometer, wherein said relative abundance value is derived from information comprising a plurality of said peak areas of the selective ion chromatograms; and (h) comparing said value of said at least one organic species of the admixture sample to the corresponding relative abundance value of the corresponding at least one organic species of the reference admixture.

55. A method of comparing a first admixture of organic species to a second admixture of organic species, comprising the steps of:

(a) fractionating the organic species of each of the first and second admixtures;

(b) subjecting each of the fractionated organic species of the first and second admixtures to mass spectroscopic analysis in order to generate a mass spectroscopic data set for the fractionated organic species of each admixture from which a plurality of selective ion chromatograms for the fractionated organic species of each admixture can be computed;

(c) computing a first plurality of selective ion chromatograms for the fractionated organic species of the first admixture, wherein the first plurality of selective ion chromatograms is derived from the mass spectroscopic data set generated for the organic species of the first admixture;

(d) computing a second plurality of selective ion chromatograms for the fractionated organic species of the second admixture, wherein the second plurality of selective ion chromatograms is derived from the mass spectroscopic data set generated for the organic species of the second admixture;

(e) automatically locating chromatographic peaks of the first and second pluralities of selective ion chromatograms;

(f) automatically matching peaks between the first and second pluralities of selective ion chromatograms in order to identify matching peak pairs; and (g) outputting information indicating results of said peak matching.

* * * * *

UNITED STATES PATENT AND TRADEMARK OFFICE
CERTIFICATE OF CORRECTION

PATENT NO. : 5,885,841

DATED : March 23, 1999

INVENTOR(S) : Richard E. Higgs, Jr., Randall K. Julian, Jr., Raymond E. Kaiser, Jr.

It is certified that an error appears in the above-identified patent and that said Letters Patent is hereby corrected as shown below:

Column 32, line 53 reads ..."52. A method for"... should read --52. An apparatus for--

Signed and Sealed this

Nineteenth Day of October, 1999

Attest:

Q. TODD DICKINSON

Attesting Officer

Acting Commissioner of Patents and Trademarks